United States Patent
Prechtel et al.

(10) Patent No.: US 9,572,751 B2
(45) Date of Patent: *Feb. 21, 2017

(54) EXTENSIBLE INTERNAL BOLSTER FOR A MEDICAL DEVICE

(71) Applicant: C. R. Bard, Inc., Murray Hill, NJ (US)

(72) Inventors: Ericka J. Prechtel, Salt Lake City, UT (US); David L. Thorne, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/270,199

(22) Filed: May 5, 2014

(65) Prior Publication Data

US 2014/0243785 A1    Aug. 28, 2014

Related U.S. Application Data

(63) Continuation of application No. 12/831,644, filed on Jul. 7, 2010, now Pat. No. 8,715,244.
(Continued)

(51) Int. Cl.
*A61M 5/32*    (2006.01)
*A61J 15/00*    (2006.01)
*A61M 39/02*    (2006.01)

(52) U.S. Cl.
CPC ......... *A61J 15/0034* (2013.01); *A61J 15/0038* (2013.01); *A61J 15/0065* (2013.01);
(Continued)

(58) Field of Classification Search
CPC ............. A61M 2039/0255; A61M 2039/0261; A61M 2202/0482; A61M 2210/1053; A61M 39/0247; A61J 15/0034; A61J 15/0015; A61J 15/0038; A61J 15/0065
See application file for complete search history.

(56) References Cited

U.S. PATENT DOCUMENTS 1,719,428 A    7/1929    Friedman
2,230,226 A    2/1941    Auzin
(Continued)

FOREIGN PATENT DOCUMENTS

EP    0930083 A2    7/1999
EP    1623693 A1    2/2006
(Continued)

OTHER PUBLICATIONS

U.S. Appl. No. 11/629,724, filed Jun. 29, 2005 Notice of Allowance dated Jun. 23, 2014.
(Continued)

*Primary Examiner* — Rebecca E Eisenberg
(74) *Attorney, Agent, or Firm* — Rutan & Tucker, LLP

(57) ABSTRACT

An internal bolster for use securing a medical device, such as a feeding tube, within a body of a patient is disclosed. In one embodiment, a feeding tube includes an internal bolster, comprising one or more bolster arms that each include a first end hingedly connected to a distal end of the medical device and a free second end. The bolster arms are selectively deployable between a first position wherein the bolster arms are substantially in-line with an axis of feeding tube, and a second position wherein the bolster arms are substantially deflected from the axis of the feeding tube to enable securement of the feeding tube within a stoma or other opening defined in the body. Various means for selectively moving the bolster arms between the first and second positions are disclosed. Related methods of use are also disclosed.

21 Claims, 24 Drawing Sheets

Related U.S. Application Data

(60) Provisional application No. 61/223,562, filed on Jul. 7, 2009.

(52) U.S. Cl.
CPC ...... *A61M 39/0247* (2013.01); *A61J 15/0015* (2013.01); *A61M 2039/0255* (2013.01); *A61M 2039/0261* (2013.01); *A61M 2039/0273* (2013.01); *A61M 2202/0482* (2013.01); *A61M 2210/1053* (2013.01)

(56) References Cited

U.S. PATENT DOCUMENTS

| | | |
|---|---|---|
| 3,108,595 A | 10/1963 | Overment |
| 3,111,930 A | 11/1963 | Zipper |
| 3,241,514 A | 3/1966 | Grimland |
| 3,397,699 A | 8/1968 | Kohl |
| 3,543,759 A | 12/1970 | McWhorter |
| 3,692,029 A | 9/1972 | Adair |
| 3,731,691 A | 5/1973 | Chen |
| 3,915,171 A | 10/1975 | Shermeta |
| 4,016,885 A | 4/1977 | Bruner |
| 4,043,338 A | 8/1977 | Homm et al. |
| 4,134,407 A | 1/1979 | Elam |
| 4,143,651 A | 3/1979 | Patel |
| 4,177,815 A | 12/1979 | Patel |
| 4,227,293 A | 10/1980 | Taylor |
| 4,245,639 A | 1/1981 | La Rosa |
| 4,366,708 A | 1/1983 | Warihashi |
| 4,370,982 A | 2/1983 | Reilly |
| 4,398,542 A | 8/1983 | Cunningham et al. |
| 4,535,757 A | 8/1985 | Webster, Jr. |
| 4,583,917 A | 4/1986 | Shah |
| 4,592,747 A | 6/1986 | Pool |
| 4,606,347 A | 8/1986 | Fogarty et al. |
| 4,608,965 A | 9/1986 | Anspach, Jr. et al. |
| 4,617,015 A | 10/1986 | Foltz |
| 4,666,433 A | 5/1987 | Parks |
| 4,685,901 A | 8/1987 | Parks |
| 4,701,163 A | 10/1987 | Parks |
| 4,729,706 A | 3/1988 | Peterson et al. |
| 4,744,788 A | 5/1988 | Mercer, Jr. |
| 4,795,430 A | 1/1989 | Quinn et al. |
| 4,798,592 A | 1/1989 | Parks |
| 4,863,438 A | 9/1989 | Gauderer et al. |
| 4,872,483 A | 10/1989 | Shah |
| 4,929,236 A | 5/1990 | Sampson |
| 4,944,732 A | 7/1990 | Russo |
| 4,981,471 A | 1/1991 | Quinn et al. |
| 4,994,034 A | 2/1991 | Botich et al. |
| 5,007,900 A | 4/1991 | Picha et al. |
| 5,071,405 A | 12/1991 | Piontek et al. |
| 5,073,166 A | 12/1991 | Parks et al. |
| 5,111,310 A | 5/1992 | Parker et al. |
| 5,112,310 A | 5/1992 | Grobe |
| 5,163,949 A | 11/1992 | Bonutti |
| 5,178,423 A | 1/1993 | Combeau |
| 5,203,773 A | 4/1993 | Green |
| 5,218,970 A | 6/1993 | Turnbull et al. |
| 5,226,876 A | 7/1993 | Filipi et al. |
| 5,232,451 A | 8/1993 | Freitas et al. |
| 5,234,454 A | 8/1993 | Bangs |
| 5,248,302 A | 9/1993 | Patrick et al. |
| 5,255,670 A | 10/1993 | Lomholt |
| 5,273,529 A | 12/1993 | Idowu |
| 5,275,610 A | 1/1994 | Eberbach |
| 5,279,564 A | 1/1994 | Taylor |
| 5,308,325 A | 5/1994 | Quinn et al. |
| 5,309,906 A | 5/1994 | LaBombard |
| 5,324,262 A | 6/1994 | Fischell et al. |
| 5,342,321 A | 8/1994 | Potter |
| 5,344,439 A | 9/1994 | Otten |
| 5,365,967 A | 11/1994 | Moore |
| 5,399,173 A | 3/1995 | Parks et al. |
| 5,403,290 A | 4/1995 | Noble |
| 5,411,491 A | 5/1995 | Goldhardt et al. |
| 5,429,598 A | 7/1995 | Waxman et al. |
| 5,429,605 A | 7/1995 | Richling et al. |
| 5,439,444 A | 8/1995 | Andersen et al. |
| 5,458,572 A | 10/1995 | Campbell et al. |
| 5,458,583 A | 10/1995 | McNeely et al. |
| 5,462,528 A | 10/1995 | Roewer |
| 5,462,561 A | 10/1995 | Voda |
| 5,470,314 A | 11/1995 | Walinsky |
| 5,514,112 A | 5/1996 | Chu et al. |
| 5,522,961 A | 6/1996 | Leonhardt |
| 5,527,280 A | 6/1996 | Goelz |
| 5,549,657 A | 8/1996 | Stern et al. |
| D373,418 S | 9/1996 | Szpak |
| 5,556,385 A | 9/1996 | Andersen |
| 5,681,280 A | 10/1997 | Rusk et al. |
| 5,720,734 A | 2/1998 | Copenhaver et al. |
| 5,749,852 A | 5/1998 | Schwab et al. |
| 5,792,119 A | 8/1998 | Marx |
| 5,836,924 A | 11/1998 | Kelliher et al. |
| 5,840,065 A | 11/1998 | Goldhardt et al. |
| 5,860,960 A | 1/1999 | Quinn |
| 5,910,128 A | 6/1999 | Quinn |
| 5,935,107 A | 8/1999 | Taylor et al. |
| 5,941,855 A | 8/1999 | Picha et al. |
| 5,993,473 A | 11/1999 | Chan et al. |
| 5,997,503 A | 12/1999 | Willis et al. |
| 5,997,546 A | 12/1999 | Foster et al. |
| 6,033,379 A | 3/2000 | Barra et al. |
| 6,045,536 A | 4/2000 | Meier et al. |
| 6,050,987 A | 4/2000 | Rosenbaum |
| 6,066,112 A | 5/2000 | Quinn |
| 6,066,155 A | 5/2000 | Amann et al. |
| 6,077,243 A | 6/2000 | Quinn |
| 6,113,572 A | 9/2000 | Gailey et al. |
| 6,113,579 A | 9/2000 | Eidenschink et al. |
| 6,149,575 A | 11/2000 | Leonhardt |
| 6,186,985 B1 | 2/2001 | Snow |
| 6,221,042 B1 | 4/2001 | Adams |
| 6,228,063 B1 | 5/2001 | Aboul-Hosn |
| 6,264,631 B1 | 7/2001 | Willis et al. |
| 6,315,789 B1 | 11/2001 | Cragg |
| 6,319,244 B2 | 11/2001 | Suresh et al. |
| 6,432,080 B2 | 8/2002 | Pederson, Jr. et al. |
| 6,506,179 B1 | 1/2003 | Tiefenthal et al. |
| 6,530,898 B1 | 3/2003 | Nimkar et al. |
| 6,565,536 B1 | 5/2003 | Sohn |
| 6,582,395 B1 | 6/2003 | Burkett et al. |
| 6,595,971 B1 | 7/2003 | von Dyck et al. |
| 6,632,197 B2 | 10/2003 | Lyon |
| 6,641,177 B1 | 11/2003 | Pinciaro |
| 6,666,853 B2 | 12/2003 | Chu et al. |
| 6,669,681 B2 | 12/2003 | Jepson et al. |
| 6,702,336 B1 | 3/2004 | Chelchowski et al. |
| 6,705,320 B1 | 3/2004 | Anderson |
| 6,732,734 B2 | 5/2004 | Ogushi et al. |
| D490,890 S | 6/2004 | Li |
| 6,858,019 B2 | 2/2005 | McGuckin, Jr. et al. |
| 6,878,130 B2 | 4/2005 | Fournie et al. |
| 6,896,665 B2 | 5/2005 | Picha et al. |
| 6,916,307 B2 | 7/2005 | Willis et al. |
| 6,929,621 B2 * | 8/2005 | Whitmore ......... A61M 25/0017 604/109 |
| 6,960,222 B2 | 11/2005 | Vo et al. |
| 6,976,980 B2 | 12/2005 | Brenner et al. |
| 6,997,909 B2 | 2/2006 | Goldberg |
| 7,008,438 B2 | 3/2006 | O'Brien |
| 7,008,441 B2 | 3/2006 | Zucker |
| 7,041,083 B2 | 5/2006 | Chu et al. |
| 7,060,050 B2 | 6/2006 | Kliem et al. |
| 7,070,587 B2 | 7/2006 | Meier |
| 7,124,489 B2 | 10/2006 | Triebes et al. |
| 7,186,238 B2 | 3/2007 | Elbert et al. |
| 7,220,243 B2 | 5/2007 | Bonnette et al. |
| 7,341,284 B2 | 3/2008 | Mittersteiner et al. |
| 7,534,224 B2 | 5/2009 | Triebes et al. |
| 7,547,303 B2 | 6/2009 | DeLegge |
| 7,582,072 B2 | 9/2009 | McMichael |

(56) References Cited

U.S. PATENT DOCUMENTS

| | | |
|---|---|---|
| 7,621,903 B2 | 11/2009 | DeLegge |
| 7,625,361 B2 | 12/2009 | Suzuki et al. |
| 7,628,775 B2 | 12/2009 | Adams et al. |
| 7,819,840 B2 | 10/2010 | Burnside et al. |
| 8,206,347 B2 | 6/2012 | Burnside et al. |
| 8,226,632 B2 | 7/2012 | Zawacki et al. |
| 8,715,244 B2 | 5/2014 | Prechtel et al. |
| 8,858,533 B2 | 10/2014 | Downing et al. |
| 2002/0093199 A1 | 7/2002 | Le |
| 2003/0055454 A1 | 3/2003 | Zucker |
| 2003/0088213 A1 | 5/2003 | Schweikert et al. |
| 2003/0120260 A1 | 6/2003 | Chu et al. |
| 2003/0212385 A1 | 11/2003 | Brenner et al. |
| 2003/0225376 A1 | 12/2003 | Fournie et al. |
| 2004/0041399 A1 | 3/2004 | Chelchowski et al. |
| 2004/0087984 A1 | 5/2004 | Kupiecki et al. |
| 2004/0103518 A1 | 6/2004 | Triebes et al. |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0147874 A1 | 7/2004 | Kliem et al. |
| 2004/0181235 A1 | 9/2004 | Daignault et al. |
| 2005/0038381 A1 | 2/2005 | McMichael |
| 2005/0200122 A1 | 9/2005 | Mittersteiner et al. |
| 2005/0267415 A1 | 12/2005 | Jacques |
| 2006/0206095 A1 | 9/2006 | Chu et al. |
| 2006/0270989 A1 | 11/2006 | McMichael et al. |
| 2006/0276746 A1 | 12/2006 | Burnside et al. |
| 2007/0021771 A1 | 1/2007 | Oepen et al. |
| 2007/0088259 A1 | 4/2007 | Chu et al. |
| 2007/0123842 A1 | 5/2007 | Teague et al. |
| 2007/0244426 A1 | 10/2007 | Hart et al. |
| 2007/0255209 A1 | 11/2007 | Crooms et al. |
| 2007/0276356 A1 | 11/2007 | Downing et al. |
| 2008/0058730 A1 | 3/2008 | Melsheimer |
| 2008/0188897 A1 | 8/2008 | Krebs et al. |
| 2009/0112183 A1 | 4/2009 | Jacques |
| 2009/0254114 A1 | 10/2009 | Hirszowicz et al. |
| 2009/0318873 A1 | 12/2009 | Bailey |
| 2010/0004601 A1 | 1/2010 | Deckard |
| 2010/0010448 A1 | 1/2010 | Deckard |
| 2010/0057013 A1 | 3/2010 | Harada |
| 2010/0185155 A1 | 7/2010 | McMichael et al. |
| 2010/0312192 A1 | 12/2010 | Fitzgerald et al. |
| 2011/0009828 A1 | 1/2011 | Prechtel et al. |
| 2011/0152762 A1 | 6/2011 | Hershey et al. |
| 2011/0196341 A1 | 8/2011 | Howell |
| 2012/0053485 A1 | 3/2012 | Bloom |
| 2012/0238959 A1 | 9/2012 | Thorne et al. |
| 2012/0245519 A1 | 9/2012 | Rotella et al. |
| 2015/0025476 A1 | 1/2015 | Downing et al. |

FOREIGN PATENT DOCUMENTS

| | | |
|---|---|---|
| EP | 2060293 A1 | 5/2009 |
| EP | 2451512 A1 | 5/2012 |
| JP | H05-115429 A | 5/1993 |
| JP | H08-506249 A | 7/1996 |
| JP | 2000-515797 T | 11/2000 |
| JP | 2006-035001 A | 2/2006 |
| JP | 2006-296794 A | 11/2006 |
| JP | 2009-534111 A | 9/2009 |
| JP | 4988725 B2 | 8/2012 |
| JP | 2012192182 A | 10/2012 |
| JP | 5184512 | 4/2013 |
| JP | 2013-518697 A | 5/2013 |
| WO | 9819730 A1 | 5/1998 |
| WO | 9852631 A1 | 11/1998 |
| WO | 02087492 A1 | 11/2002 |
| WO | 2004050009 A1 | 6/2004 |
| WO | 2006-111416 A1 | 10/2006 |
| WO | 2007087254 A2 | 8/2007 |
| WO | 2007-124167 A2 | 11/2007 |
| WO | 2009135141 A1 | 11/2009 |
| WO | 2011005847 A1 | 1/2011 |
| WO | 2011100310 A2 | 8/2011 |

OTHER PUBLICATIONS

U.S. Appl. No. 12/265,102, filed Nov. 5, 2008 Final Office Action dated May 27, 2015.
U.S. Appl. No. 12/265,102, filed Nov. 5, 2008 Non-Final Office Action dated Dec. 9, 2014.
U.S. Appl. No. 13/024,046, filed Feb. 9, 2011 Final Office Action dated Jun. 26, 2014.
U.S. Appl. No. 13/024,046, filed Feb. 9, 2011 Final Office Action dated May 4, 2015.
U.S. Appl. No. 13/024,046, filed Feb. 9, 2011 Non-Final Office Action dated Dec. 9, 2014.
U.S. Appl. No. 13/419,185, filed Mar. 13, 2012 Advisory Action dated Jul. 16, 2014.
U.S. Appl. No. 13/419,185, filed Mar. 13, 2012 Final Office Action dated May 5, 2014.
U.S. Appl. No. 13/419,185, filed Mar. 13, 2012 Non-Final Office Action dated Jan. 2, 2015.
U.S. Appl. No. 13/419,185, filed Mar. 13, 2012 Non-Final Office Action dated Sep. 3, 2013.
EP 11742731.0 filed Sep. 4, 2012 extended European Search Report dated Aug. 6, 2013.
JP 2007-519438 filed Jun. 29, 2005 Decision to Grant dated Sep. 4, 2012.
JP 2007-519438 filed Jun. 29, 2005 Office Action dated Nov. 30, 2010.
Michaud, Laurent et al, Longevity of Balloon-Stabilized Skin-Level Gastrostomy Device, Journal of Pediatric Gastroenterology and Nutrition, 38: 426-429; Apr. 2004.
PCT/US11/24176 filed Feb. 9, 2011 International Preliminary Report on Patentability dated Oct. 11, 2012.
PCT/US11/24176 filed Feb. 9, 2011 International Search Report and Written Opinion dated Jul. 8, 2011.
PCT/US2005/023297 filed Jun. 29, 2005 International Preliminary Report on Patentability dated Jan. 9, 2007.
PCT/US2005/023297 filed Jun. 29, 2005 Search Report dated May 26, 2006.
PCT/US2005/023297 filed Jun. 29, 2005 Written Opinion dated May 26, 2006.
PCT/US2006/022020 filed Jun. 6, 2006 International Preliminary Report on Patentability dated Dec. 6, 2007.
PCT/US2006/022020 filed Jun. 6, 2006 Search Report dated Jan. 25, 2007.
PCT/US2006/022020 filed Jun. 6, 2006 Written Opinion dated Jan. 25, 2007.
PCT/US2010/041192 filed Jul. 7, 2010 International Search Report dated Sep. 20, 2010.
PCT/US2010/041192 filed Jul. 7, 2010 Written Opinion dated Sep. 20, 2010.
U.S. Appl. No. 11/127,662, filed May 12, 2005 Advisory Action dated May 16, 2008.
U.S. Appl. No. 11/127,662, filed May 12, 2005 Final Office Action dated Mar. 5, 2008.
U.S. Appl. No. 11/127,662, filed May 12, 2005 Final Office Action dated Mar. 6, 2007.
U.S. Appl. No. 11/127,662, filed May 12, 2005 Non-Final Office Action dated Aug. 9, 2007.
U.S. Appl. No. 11/127,662, filed May 12, 2005 Non-Final Office Action dated Jul. 9, 2008.
U.S. Appl. No. 11/127,662, filed May 12, 2005 Non-Final Office Action dated Oct. 17, 2006.
U.S. Appl. No. 11/422,559, filed Jun. 6, 2006 Final Office Action dated Apr. 2, 2009.
U.S. Appl. No. 11/422,559, filed Jun. 6, 2006 Non-Final Office Action dated Aug. 8, 2008.
U.S. Appl. No. 11/422,559, filed Jun. 6, 2006 Non-Final Office Action dated Jan. 6, 2010.

(56) References Cited

OTHER PUBLICATIONS

U.S. Appl. No. 11/422,559, filed Jun. 6, 2006 Notice of Allowance dated Jun. 24, 2010.
U.S. Appl. No. 11/629,724, filed Jun. 29, 2005 Non-Final Office Action dated Aug. 26, 2008.
U.S. Appl. No. 11/629,724, filed Jun. 29, 2005 Final Office Action dated Jan. 4, 2011.
U.S. Appl. No. 11/629,724, filed Jun. 29, 2005 Final Office Action dated May 4, 2010.
U.S. Appl. No. 11/629,724, filed Jun. 29, 2005 Non-Final Office Action dated Feb. 28, 2014.
U.S. Appl. No. 11/629,724, filed Jun. 29, 2005 Non-Final Office Action dated Jul. 22, 2010.
U.S. Appl. No. 11/629,724, filed Jun. 29, 2005 Non-Final Office Action dated Oct. 2, 2009.
U.S. Appl. No. 11/738,979, filed Apr. 23, 2007 Final Office Action dated Jan. 13, 2012.
U.S. Appl. No. 11/738,979, filed Apr. 23, 2007 Notice of Allowance dated Jun. 17, 2013.
U.S. Appl. No. 11/738,979, filed Apr. 23, 2007 Advisory Action dated Jun. 18, 2009.
U.S. Appl. No. 11/738,979, filed Apr. 23, 2007 Final Office Action dated Apr. 16, 2009.
U.S. Appl. No. 11/738,979, filed Apr. 23, 2007 Final Office Action dated Jan. 25, 2010.
U.S. Appl. No. 11/738,979, filed Apr. 23, 2007 Non-Final Office Action dated Nov. 24, 2008.
U.S. Appl. No. 11/738,979, filed Apr. 23, 2007 Non-Final Office Action dated Oct. 9, 2009.
U.S. Appl. No. 12/265,102, filed Nov. 5, 2008 Advisory Action dated Apr. 3, 2012.
U.S. Appl. No. 12/265,102, filed Nov. 5, 2008 Final Office Action dated Jan. 13, 2012.
U.S. Appl. No. 12/265,102, filed Nov. 5, 2008 Final Office Action dated Jun. 26, 2013.
U.S. Appl. No. 12/265,102, filed Nov. 5, 2008 Non-Final Office Action dated Dec. 18, 2012.
U.S. Appl. No. 12/265,102, filed Nov. 5, 2008 Non-Final Office Action dated Jul. 29, 2011.
U.S. Appl. No. 12/831,644, filed Jul. 7, 2010 Final Office Action dated Nov. 7, 2012.
U.S. Appl. No. 12/831,644, filed Jul. 7, 2010 Non-Final Office Action dated Aug. 1, 2013.
U.S. Appl. No. 12/831,644, filed Jul. 7, 2010 Non-Final Office Action dated Mar. 30, 2012.
U.S. Appl. No. 12/831,644, filed Jul. 7, 2010 Notice of Allowance dated Dec. 26, 2013.
U.S. Appl. No. 12/902,987, filed Oct. 12, 2010 Final Office Action and Reasons for Allowance dated Dec. 22, 2011.
U.S. Appl. No. 12/902,987, filed Oct. 12, 2010 Notice of Allowance dated Dec. 22, 2011.
U.S. Appl. No. 13/024,046, filed Feb. 9, 2011 Non-Final Office Action dated Nov. 29, 2013.
U.S. Appl. No. 13/419,185, filed Mar. 13, 2012 Final Office Action dated Feb. 13, 2014.
JP 2012-057330 filed Mar. 14, 2012 First Office Action dated Jan. 28, 2016.
U.S. Appl. No. 13/419,185, filed Mar. 13, 2012 Non-Final Office Action dated Sep. 24, 2015.
U.S. Appl. No. 13/419,185, filed Mar. 13, 2012 Final Office Action dated Apr. 26, 2016.
U.S. Appl. No. 14/507,801, filed Oct. 6, 2014 Non-Final Office Action, dated Aug. 25, 2016.

\* cited by examiner

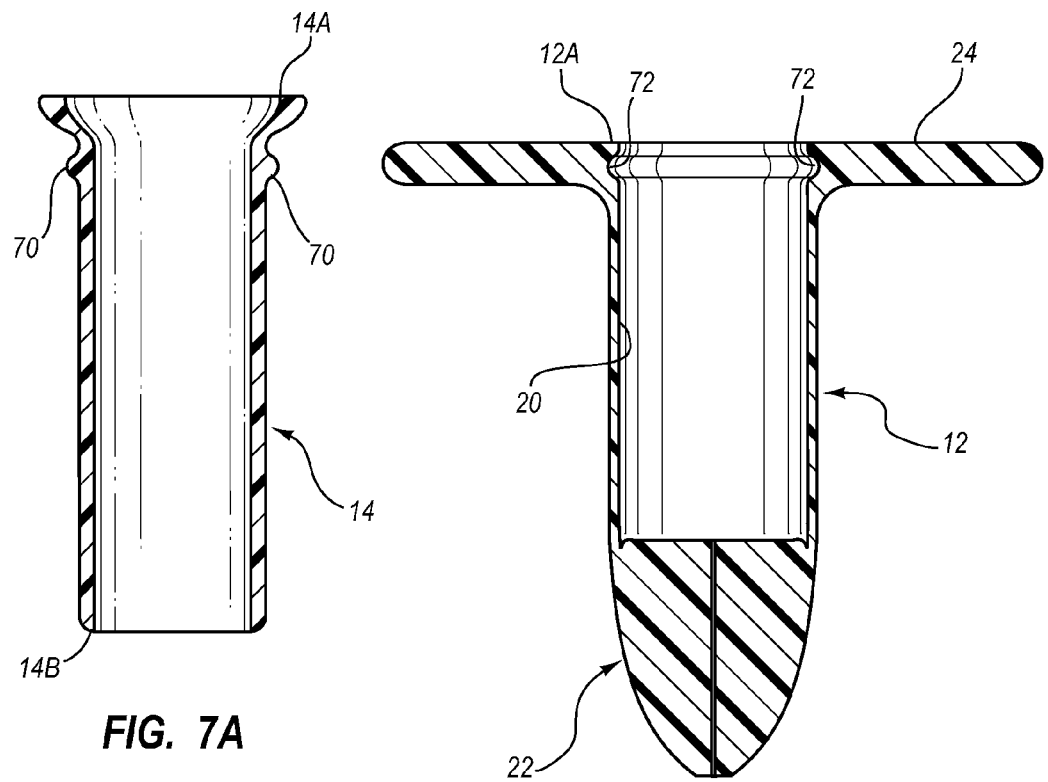
FIG. 7A
FIG. 7B
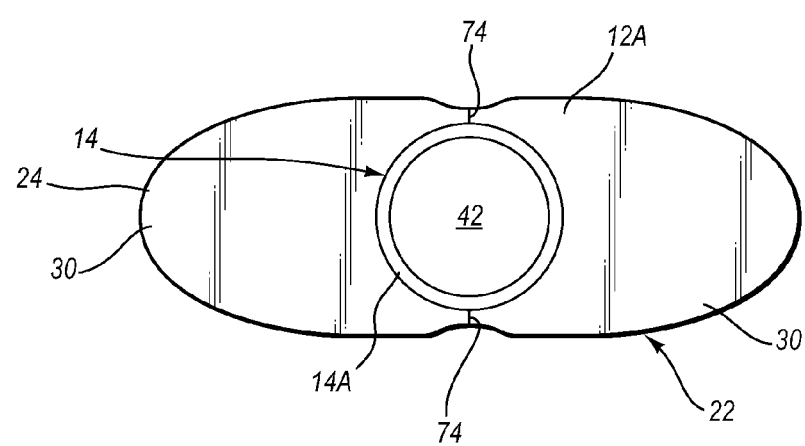
FIG. 7C

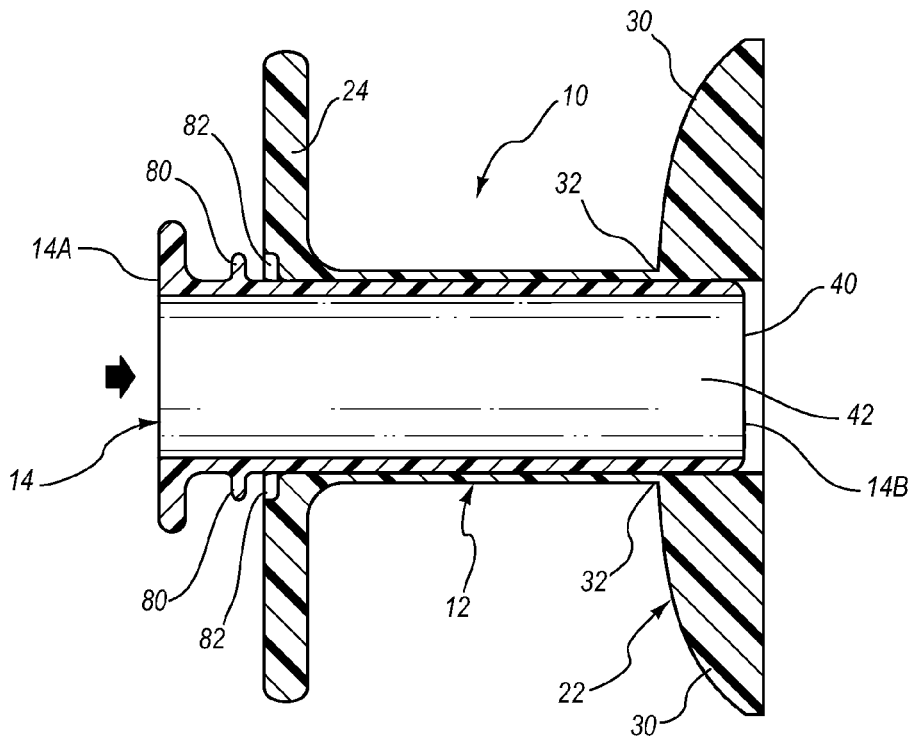
FIG. 8A
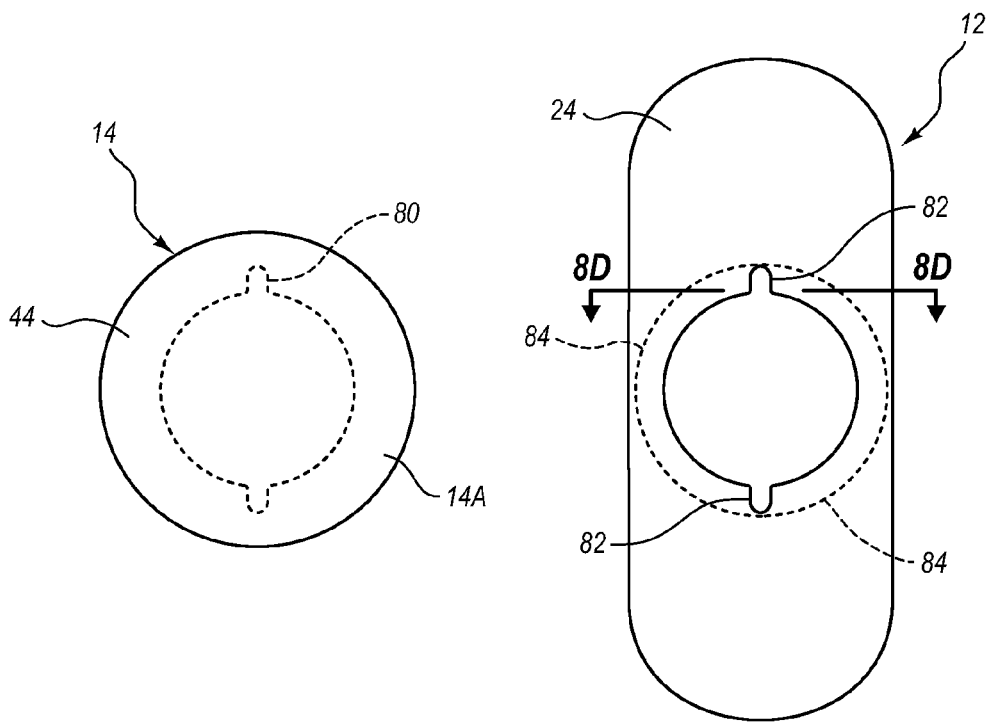
FIG. 8B  FIG. 8C

EXTENSIBLE INTERNAL BOLSTER FOR A MEDICAL DEVICE

CROSS-REFERENCE TO RELATED APPLICATIONS

This application is a continuation of U.S. patent application Ser. No. 12/831,644, filed Jul. 7, 2010, now U.S. Pat. No. 8,715,244, which claims the benefit of U.S. Provisional Application No. 61/223,562, filed Jul. 7, 2009, and titled "Feeding Device Including an Extensible Internal Bolster," each of which is incorporated herein by reference in its entirety.

BRIEF SUMMARY

Briefly summarized, embodiments of the present invention are directed to an internal bolster for use securing a medical device within a body of a patient. One example of a medical device includes a feeding tube for providing enteral nutrition to the patient, though many other medical devices can benefit from the principles to be depicted and described herein.

In one embodiment, the feeding tube includes an internal bolster, comprising one or more bolster arms that each include a first end hingedly connected to a distal end of the medical device and a free second end. The bolster arms are selectively deployable between a first position wherein the bolster arms are substantially in-line with an axis of feeding tube, and a second position wherein the bolster arms are substantially deflected from the axis of the feeding tube to enable securement of the feeding tube within a stoma or other opening defined in the body. Various means for selectively moving the bolster arms between the first and second positions are disclosed. Related methods of use for the internal bolster are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 7A-7C are various views of a feeding device such as that shown in FIG. 1A, including an interference locking mechanism in accordance with one embodiment;

FIGS. 8A-8D are various views of a feeding device such as that shown in FIG. 1A, including a tab/slot locking mechanism in accordance with one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a feeding device placed within the body of a patient is considered a distal end of the catheter, while the feeding device end remaining outside the body is a proximal end of the catheter. Also, the words "including," "has," and "having," as used herein, including the claims, shall have the same meaning as the word "comprising."

FIGS. 1A-18E depict various features of embodiments of the present invention, which are generally directed to a selectively extensible or deployable internal bolster for use in anchoring a medical device, such as a feeding tube, within a body of a patient. The internal bolster is configured to selectively deploy from collapsed state to an expanded state so as to ease both insertion and removal of a device into or from a patient, such as via a stoma. This in turn reduces patient trauma and pain during placement and removal of the device.

Figure 1A:
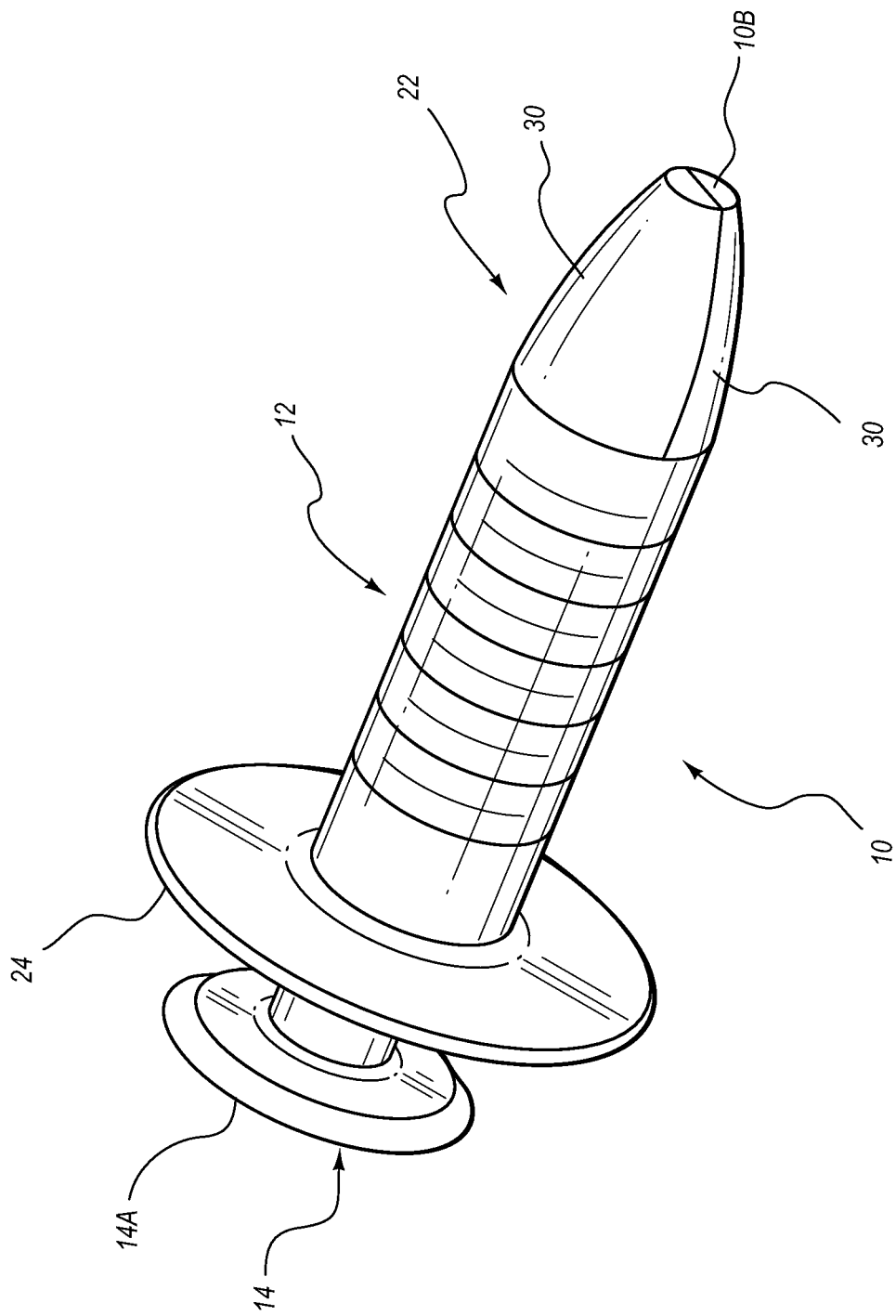
FIGS. 1A-1C are various views of a feeding device configured in accordance with one example embodiment of the present invention.
Figure 1B:
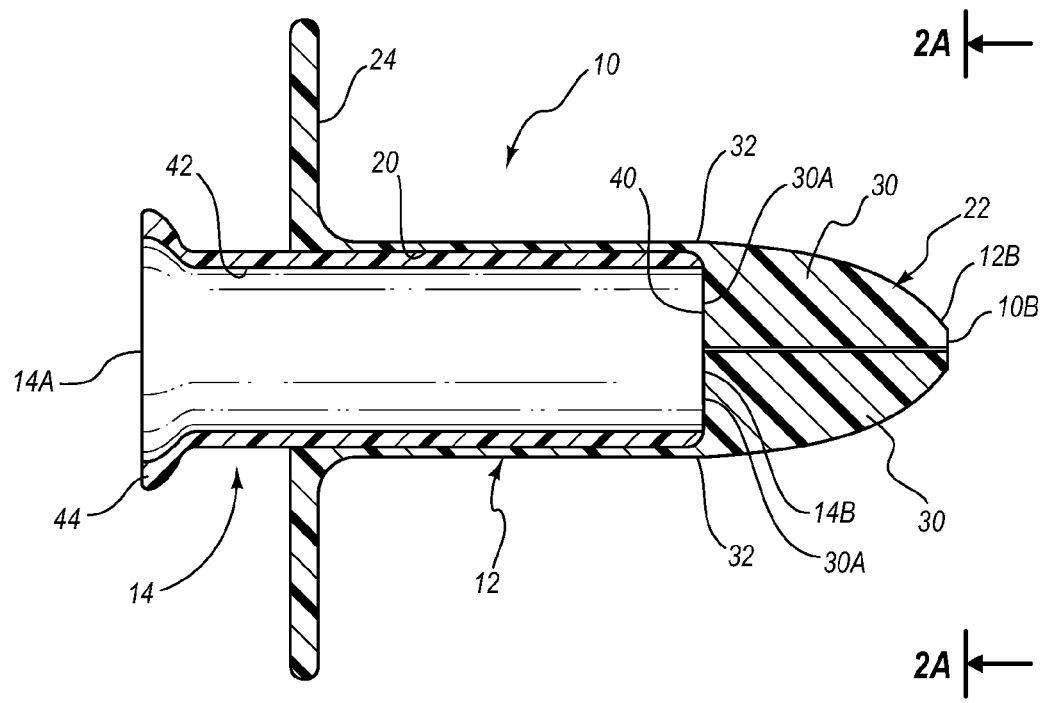
Figure 1C:
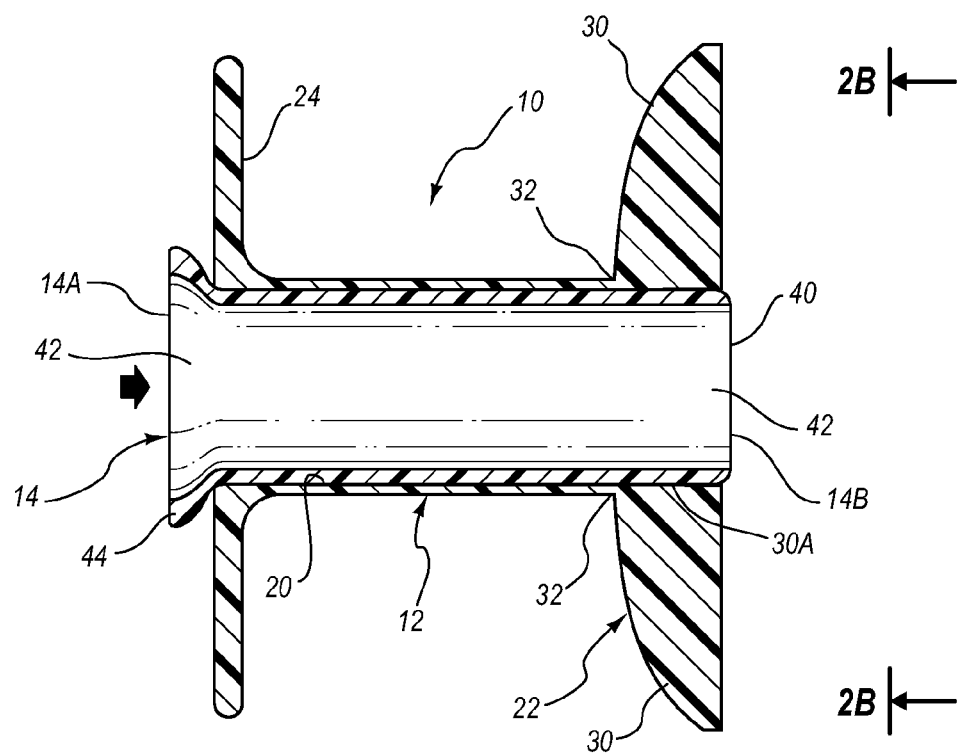

Reference is first made to FIGS. 1A-1C, which depict a feeding device, generally designated at 10, including an internal bolster configured in accordance with one example embodiment. The feeding device 10 generally includes an outer bolster tube 12 and an inner plunger 14. Including both a proximal end 14A and a distal end 14B, the plunger 14 is slidably received within an elongate cavity 20 defined by the bolster tube 12 via an opening to the cavity defined at a proximal end 12A thereof. A distal portion of the bolster tube 12 includes an internal bolster 22, while a flange 24 is included at a proximal portion of the bolster tube. The flange 24 can take one of many different configurations, including an annular shape, opposing tabs, etc.

In greater detail, the internal bolster 22 includes one or more bolster arms 30 that are each hingedly connected to a distal portion of the bolster tube 12 at a hinge point 32 via a living hinge or other suitable connection scheme. Each bolster arm 30 thus includes an end attached to the bolster tube 12 and a free end. So configured, the bolster arms 30 are pivotable about the hinge point 32 so as to be able to be selectively deployed from a first, un-deployed position shown in FIGS. 1A and 1B, i.e., the configuration for inserting or removing the feeding device via an opening or stoma defined in the patient such as to gain access to the stomach of the patient for example (similar to the insertion of the device shown in FIG. 11A), to a second, deployed position shown in FIG. 1C, i.e., the configuration wherein the bolster anchors the feeding device within the patient after insertion through the stoma (similar to the anchoring of the device shown in FIG. 11B). Note that when in the first, un-deployed position, the bolster arms 30 are contiguously disposed together in one embodiment to define an atraumatic tip for the feeding device 10 to assist in inserting the feeding device through the stoma or other opening defined in the tissue of a patient.

As best seen in FIGS. 1A and 1B the internal bolster 22, as positioned in the present embodiment, defines the distal end 10B of the feeding device 10. It is appreciated, however, that in other embodiments the internal bolster can be disposed at a point proximal to a distal end of the feeding tube or other device with which the internal bolster is included. As such, the discussion relating to the shape, design, and placement of the internal bolster embodiments described herein should not be considered limiting of the present invention in any way. Further, it is appreciated that, while shown in connection with a gastrostomy or feeding tube, the internal bolster can be included with insertable medical devices of a variety of types and configurations.

In the present embodiment, the plunger 14 of the feeding device 10 includes an engagement surface 40 at a distal end 14B thereof that is configured to actuate the bolster arms 30 of the internal bolster 22 when the plunger, received within the cavity 20 of the bolster tube 12, is pressed distally. In detail, a proximal end 14A of the plunger 14 can be manually pressed by a user to advance the plunger distally through the bolster tube cavity 20 during inner bolster actuation. The plunger proximal end 14A includes a first plunger stop 44 configured to limit distal insertion of the plunger 14 into the bolster tube cavity 20.

Distal movement of the plunger 14 with respect to the bolster tube 12 causes engagement of the plunger engagement surface 40 with a proximal base 30A of each bolster arm 30, which causes the bolster arms to hingedly pivot about the hinge point 32 and open, or deploy to the position shown in FIG. 1C. Thus, it is seen that in the un-deployed, or first, position shown in FIG. 1B, 2A a length of each bolster arm 30 is in-line, or aligned substantially parallel with a longitudinal axis of the bolster tube 12. So configured, the internal bolster 22 when in the un-deployed first position of FIG. 1B, 2A includes an outer diameter no larger than that of the bolster tube 12 to facilitate atraumatic insertion of the feeding tube 10 through the stoma. Correspondingly, in the deployed, or second, position of FIG. 1C, 2B each bolster arm opens radially outward such that the length of each bolster arm 30 is substantially non-parallel with respect to the longitudinal axis of the bolster tube 12, thus serving as a securement for preventing removal of the feeding tube 10 from a stoma or other hole through which the feeding tube is inserted. The deployability of the bolster arms 30 is selectively reversible such that withdrawal of the plunger 14 from engagement with the bases 30A of the bolster arms enables the bolster arms to return to the first position.

Note that in the present embodiment, the feeding tube is tubular and cross sectionally round; in other embodiments, however, a non-tubular or non-cross sectionally round medical device can also benefit from the principles described herein. Note further that the mode of attachment of the bolster arms to the bolster tube can include integral formation, molding or overmolding, mechanical fixation, adhesive attachment, etc.

Movement of the internal bolster 22 from the second deployed position to the first position, in preparation for removal of the feeding tube 10 for instance, is achieved via proximal movement of the plunger 14 with respect to the bolster tube 12. This movement separates the plunger engagement surface 40 from the bolster arm bases 30A, which allows the bolster arms 30 to pivot back to their un-deployed position shown in FIGS. 1B, 2A. This selective deployability of the internal bolster 22 enables the feeding device 10 to be readily inserted and removed from the patient. A channel 42 is defined by the plunger 14 therethrough so as to provide a pathway through which enteral nutrition can be provided to the patient. Valves, connectors, or other apparatus can be included with or attached to the feeding device to enable suitable access to the channel 42, and the channel can be modified from what is shown and described herein. Note that in the present embodiment, the bolster arms 30 substantially cover the distal opening feeding device 10 when in the first position (FIG. 1B), and that the distal opening is substantially uncovered when the bolster arms are in the second position (FIG. 1C).

It is thus seen that the plunger 14 described above serves as one example of a means for selectively moving the bolster arms between the first and second positions. It is appreciated that other methods and structures may be used for this purpose as may be appreciated by one skilled in the art and as seen in the discussion further below.

The bolster tube 12 and plunger 14 are sized to enable relative movement therebetween when the plunger is received within the cavity 20 of the bolster tube. Though configured as a sliding engagement in the present embodiment, the relative movement spoken of here can be implemented in other ways as well, including gear-teeth engagement, etc. The cross sectional profiles of both the bolster tube cavity 20 and the outer surface of the plunger 14 are round in the present embodiment. In other embodiments, other cross sectional shapes can be used, including square, pentagonal, oval, etc. In other embodiments, the plunger can be keyed to the bolster tube cavity so as to prevent relative rotation therebetween, if desired. In one embodiment, oil or other lubricants can be interposed between the bolster tube cavity 20 and the outer surface of the plunger 14 so as to ease relative movement therebetween.

Figure 3A:
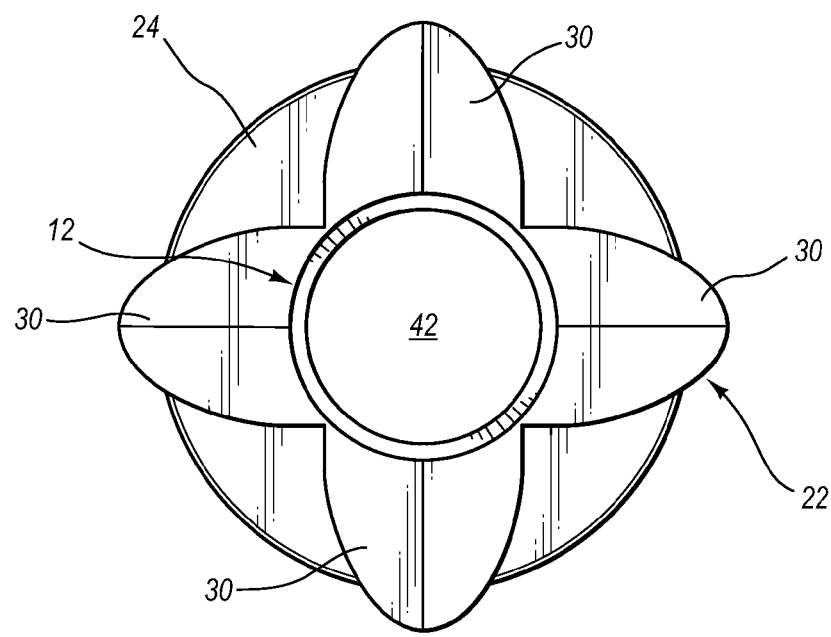
FIGS. 3A-3B are distal end views of example feeding devices such as that shown in FIG. 1A, including differing numbers of distal end internal bolster arms.
Figure 3B:
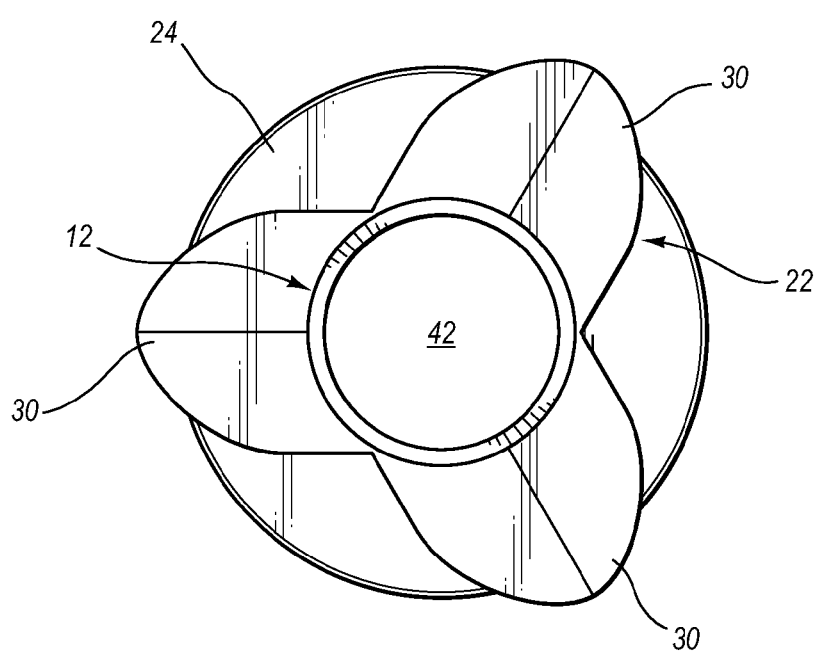

As indicated by FIGS. 3A and 3B, the number of bolster arms in the internal bolster 22 can include one, two, three, four, or more. Also, though shown here as contoured to assist in device insertion and removal, the bolster arms mutually or independently can define one of many shapes, including rectangular, round, bullet-shaped, triangular, etc. In the present embodiment both the bolster tube 12 and the plunger 14 include biocompatible materials, such as silicone for the bolster tube/bolster arms and acetyl homopolymer, e.g., an engineering plastic sold under the trademark DELRIN®, or other engineering plastic or suitable material for the plunger. As mentioned, the plunger can further include a valve for preventing inadvertent passage of material or air through the feeding device.

Note that, as indicated in FIGS. 1A-2B, the bolster arms 30 move in unison between the first and second positions. In other embodiments, however, the plunger can be configured such that the bolster arms move independently or at different stages of internal bolster deployment. This can be achieved, for instance, by including a staggered engagement surface on the distal end of the plunger or bolster arm base.

Figure 2A:
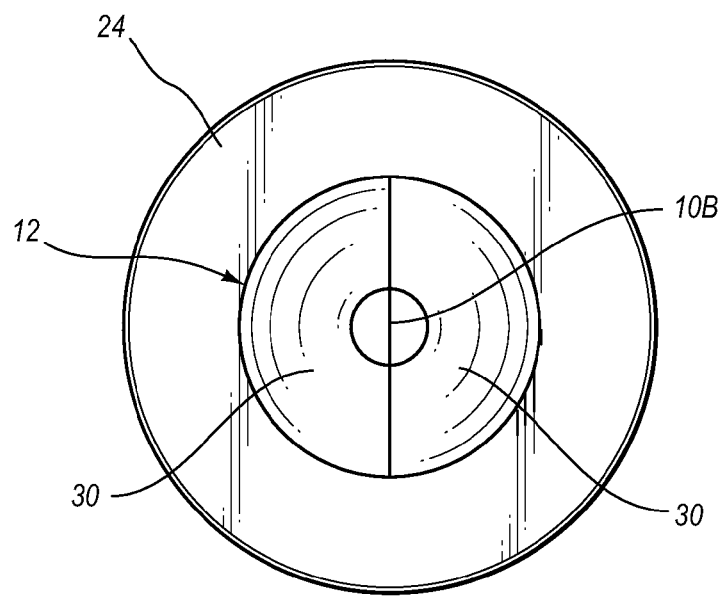
FIGS. 2A-2B are end views of the feeding device configurations shown in FIGS. 1B and 1C, respectively.
Figure 2B:
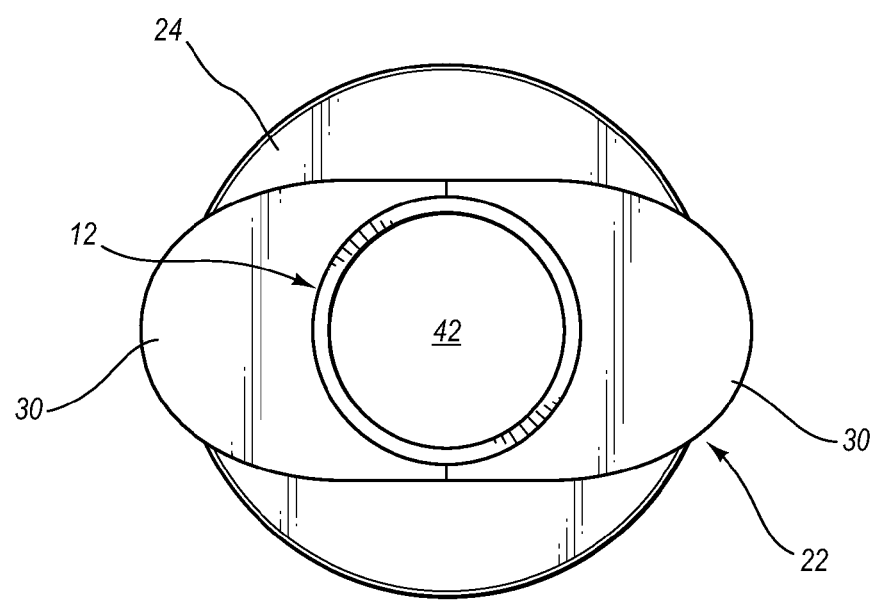
Figure 4A:
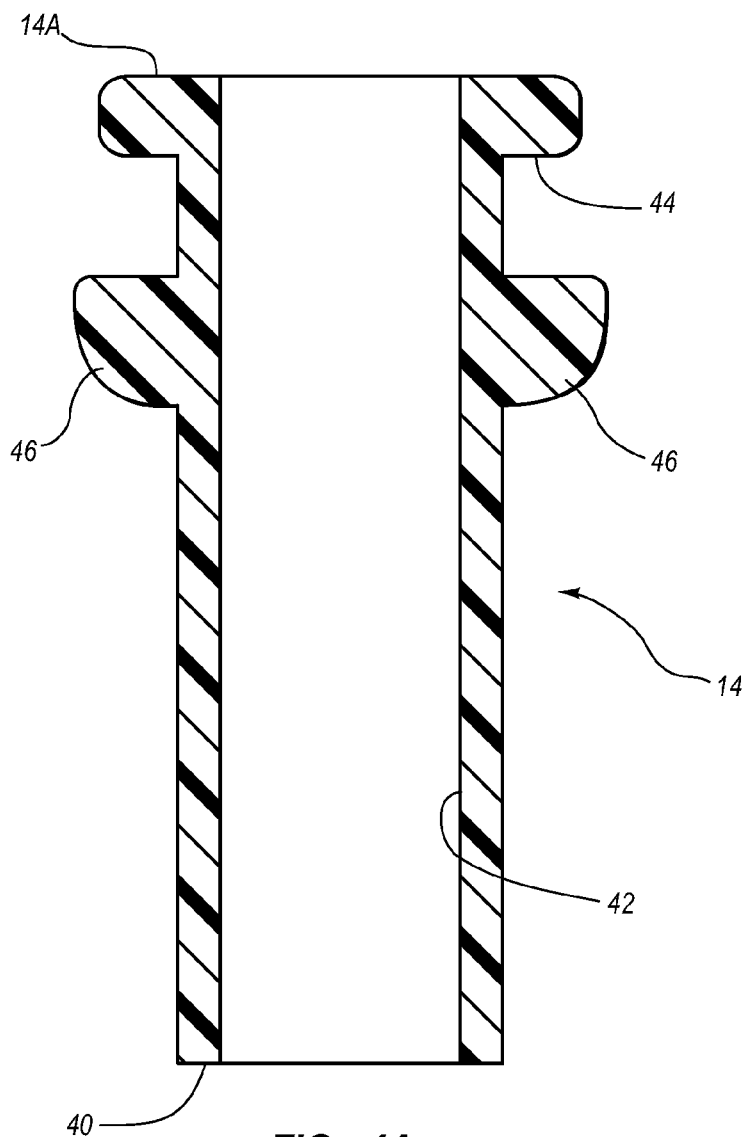
FIGS. 4A and 4B are cross sectional side and end views, respectively, of a plunger of the feeding device of FIG. 1A, according to one embodiment.
Figure 4B:
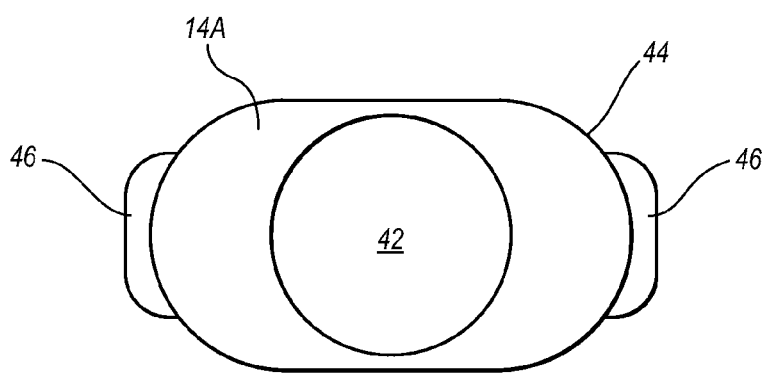

The feeding device 10 can include one of a variety of implementations for preventing unintended axial movement of the plunger 14 relative to the bolster tube 12 in order to prevent the bolster arms 30 from folding up from their deployed second position shown in FIG. 1C, 2B. One such implementation is shown in FIGS. 4A and 4B, wherein locking tabs 46 are included on an outer surface of a portion of the plunger 14 that is received by the bolster tube cavity 20. The tabs 14 are configured to be received into corresponding detents included on an inside surface of the bolster tube cavity 20 when the plunger 14 is pushed distally through the cavity in order to engage and spread open the bolster arms 30 of the internal bolster 22. Once received in the detents, the tabs 46 retain the plunger 14 within the bolster tube cavity 20 to lock it in place. Cutting of the bolster tube 12, for instance, can release the tabs 46 from the bolster tube detents in order to slide the plunger 14 relative to the bolster tube. Thus the tabs 14 and corresponding detents describe one example of means for locking axial plunger movement relative to the bolster tube 12 or other suitable device with which the plunger is included. It is appreciated that other methods and structures may be used for this purpose as may be appreciated by one skilled in the art and as seen in the below discussion.

FIGS. 7A-7C show a similar means for locking axial movement of the plunger 14 relative to the bolster tube 12, wherein an outer surface of the plunger 14 includes an annular knob 70 for engagement with a corresponding annular detent 72 defined by an inner surface of the bolster tube 12 in the cavity 20 when the plunger is inserted into the cavity to deploy the bolster arms 30. FIG. 7C is a proximal end view of the feeding device 10, showing the location of cut points 74 where the bolster tube 12 can be cut in order to separate the engagement between knob 70 and corresponding detent 72.

Figure 5:
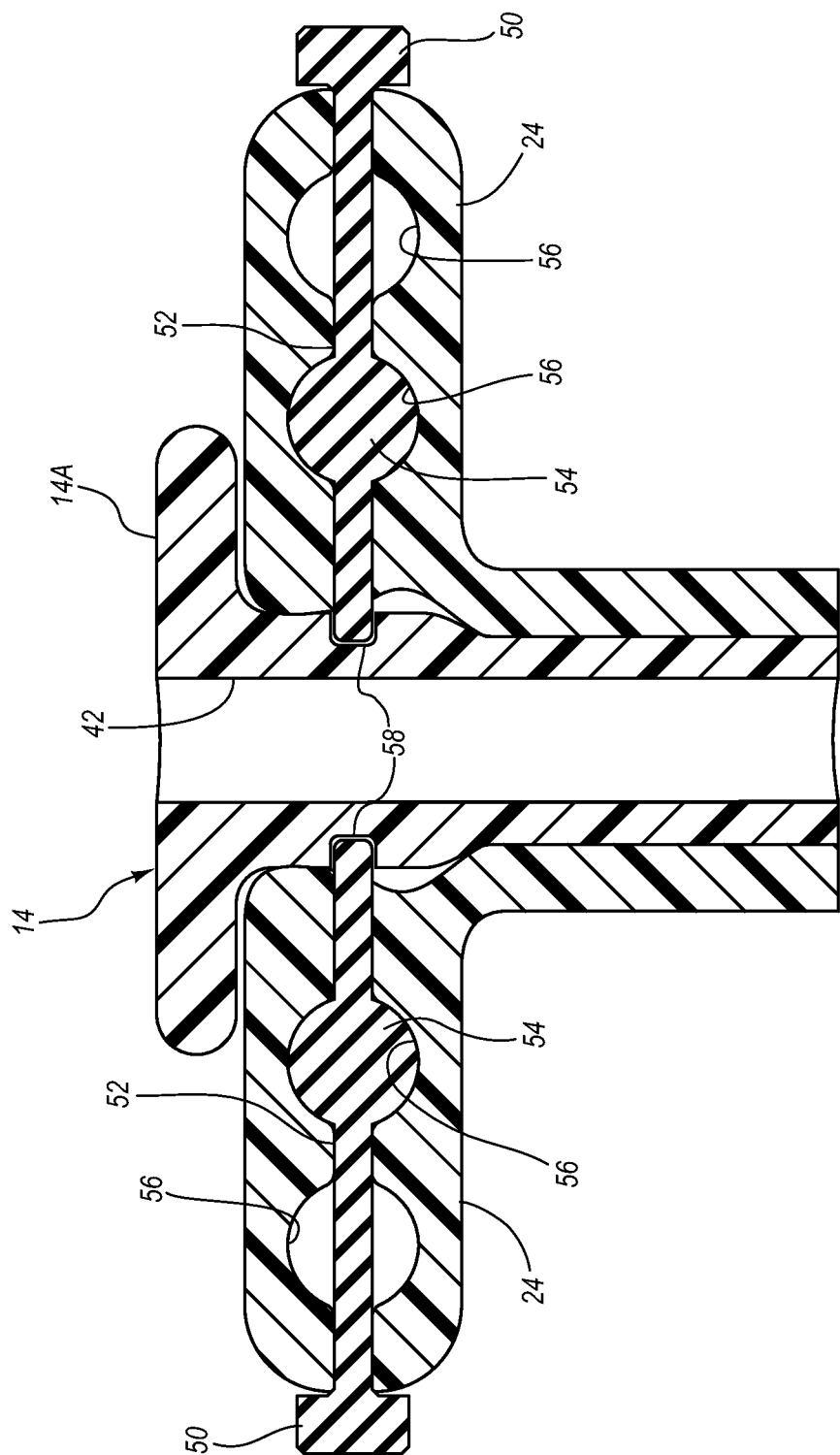
FIG. 5 is a cross sectional side view of a feeding device such as that shown in FIG. 1A, including a locking mechanism in accordance with one embodiment.

FIG. 5 shows another example of means for locking axial plunger movement relative to the bolster tube 12, wherein one or more pin channels 52 are defined by the bolster tube flange 24 and each configured for receiving a locking pin 50 therein. Each locking pin 50 includes a bump 54 that is selectively seatable in one of a plurality of detents 56 defined in the respective pin channel 52. Thus, each locking pin 50 can be selectively pushed or otherwise moved by a user between an outer one of the detents 56 to an inner detent, which action causes an inner end of the locking pin to engage a recess 58 or other suitable structure defined in an outer surface of the plunger 14, thus locking the plunger and bolster tube 12 together to prevent unintended movement therebetween when the plunger has been inserted sufficient to deploy the bolster arms 30 of the internal bolster 22. When relative plunger movement is again desired, the locking pin 50 can be pulled out to release the locking engagement and enable the plunger to be axially moved. Of course, this locking pin arrangement is merely an example of many other possible locking pin configurations that can be utilized in connection with the present feeding device. For instance, it is appreciated that a threaded locking pin and pin channel can be employed in one embodiment.

Figure 6A:
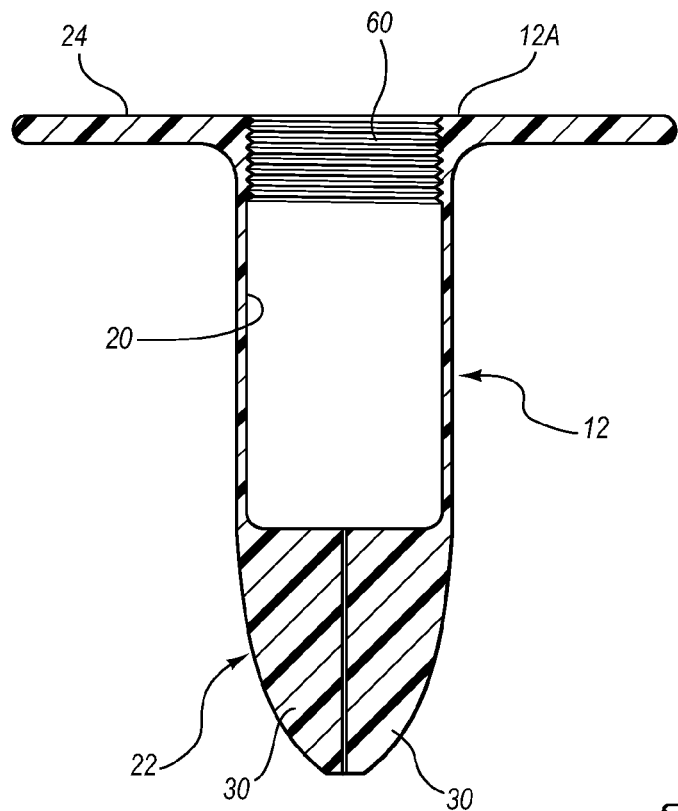
FIGS. 6A and 6B are cross sectional side views of a feeding device such as that shown in FIG. 1A, including a threaded locking mechanism in accordance with one embodiment.
Figure 6B:
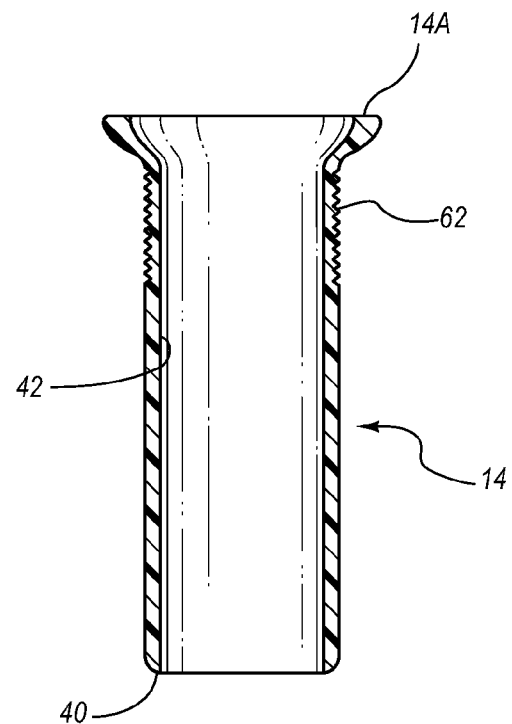

FIGS. 6A-6B depict yet another means for locking axial movement of the plunger 14 relative to the bolster tube 12, wherein corresponding threads 60 and 62 are included on an inner surface of the bolster tube cavity 20 and an outer surface of the plunger 14, respectively. So configured, the plunger 14 can be inserted into the bolster tube cavity 20 to actuate and deploy the internal bolster 22, then be rotated to threadingly engage its threads 62 with the threads 60 of the bolster tube 12 cavity, thus selectively locking the position of the two components. Should the insertion depth of the plunger 14 within the bolster tube cavity 20 need to be modified, the plunger can be selectively rotated clockwise or counter-clockwise as needed. When no rotation of the plunger 14 is made, axial movement of the plunger is prevented via engagement of the threads 60, 62.

Figure 8D:
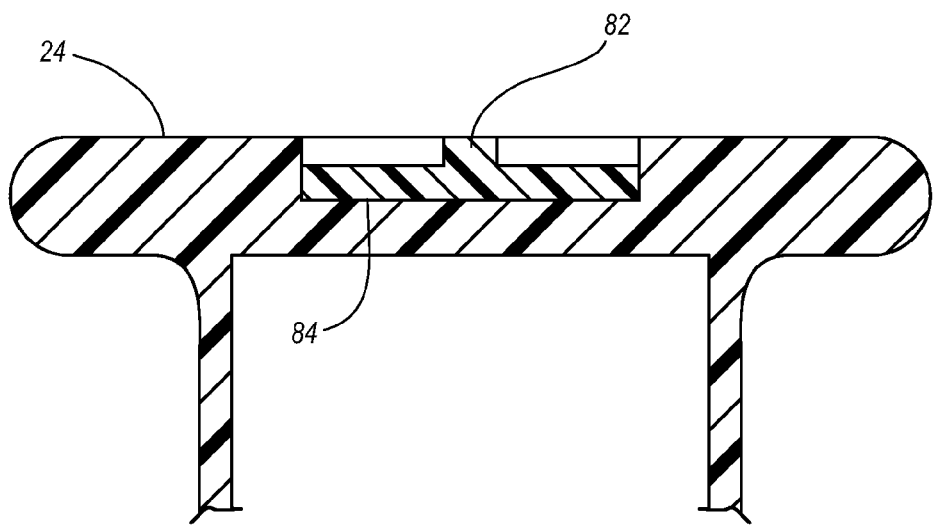

FIGS. 8A-8D show yet another means for locking axial movement of the plunger 14 relative to the bolster tube 12, wherein opposing tabs 80 are included on the plunger proximal end 14A for engagement with corresponding slots 82 defined by the bolster tube flange 24 when the plunger is inserted into the bolster tube cavity 20 in order to deploy the bolster arms 30 of the bolster tube internal bolster 22. FIGS. 8C and 8D show that each slot 82 defined in the bolster tube flange 24 is in communication with a channel 84 defined below the slots. The slots 82 enable the respective tabs 80 of the plunger 14 to be received therethrough and into the channel(s) 84 when the plunger is inserted into the bolster tube cavity 20 to deploy the internal bolster 22. Once the tabs are received into the channel(s) 84 via the slots 82, the plunger 14 is rotated about its longitudinal axis to cause the tabs to slide laterally within the channel(s) to a rest position such that the plunger is locked axially with respect to the bolster tube 12. The process can be reversed to free the plunger 14 from the bolster tube 12 in preparation of separation thereof. It is appreciated that the size, shape, and number of tabs, slots, and channels can vary from what is described herein.

Figure 8E:
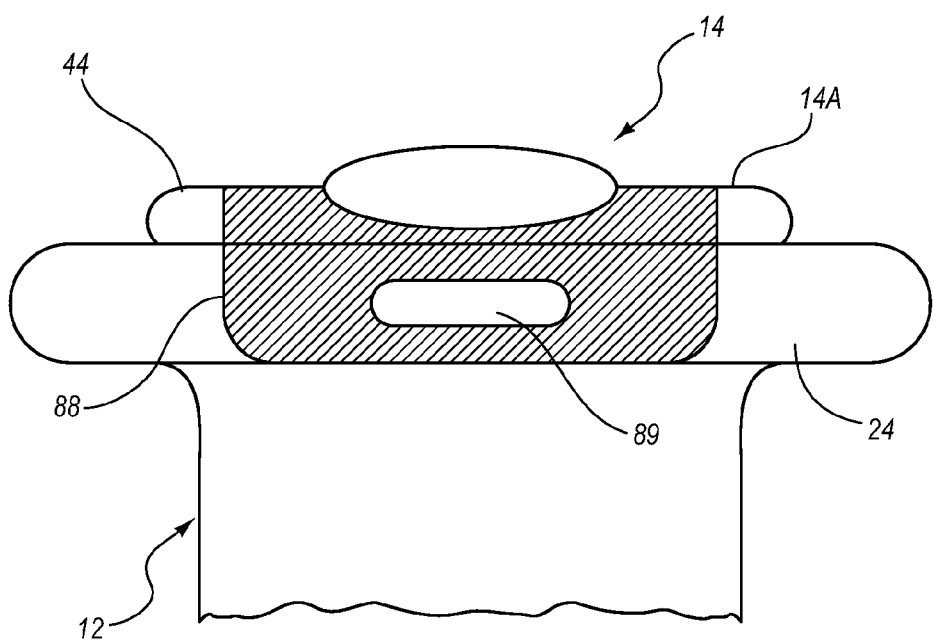
FIG. 8E is a side view of a retention cover for use with a feeding device in accordance with one embodiment.

FIG. 8E shows that an elastic cover 88 can be employed as yet another example of means for locking axial movement of the plunger 14 relative to the bolster tube 12, wherein the cover is slid over proximal portions of the plunger 14, e.g., the first plunger stop 44, and the bolster tube 12, e.g., the flange 24, to lock the two components together after deployment of the internal bolster 22. A knob 89 can be included on one of the components over which the cover 88 can be slid so as to keep the cover in place.

Figure 9A:
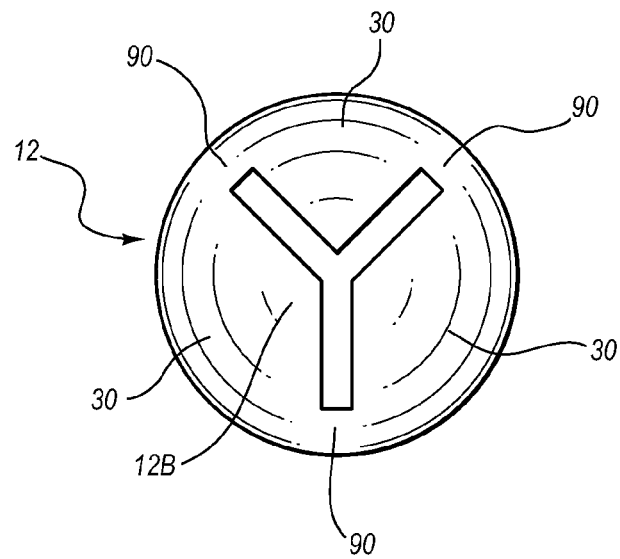
FIGS. 9A and 9B are end and side views, respectively, of a feeding device including webbing between bolster arms of the internal bolster.
Figure 9B:
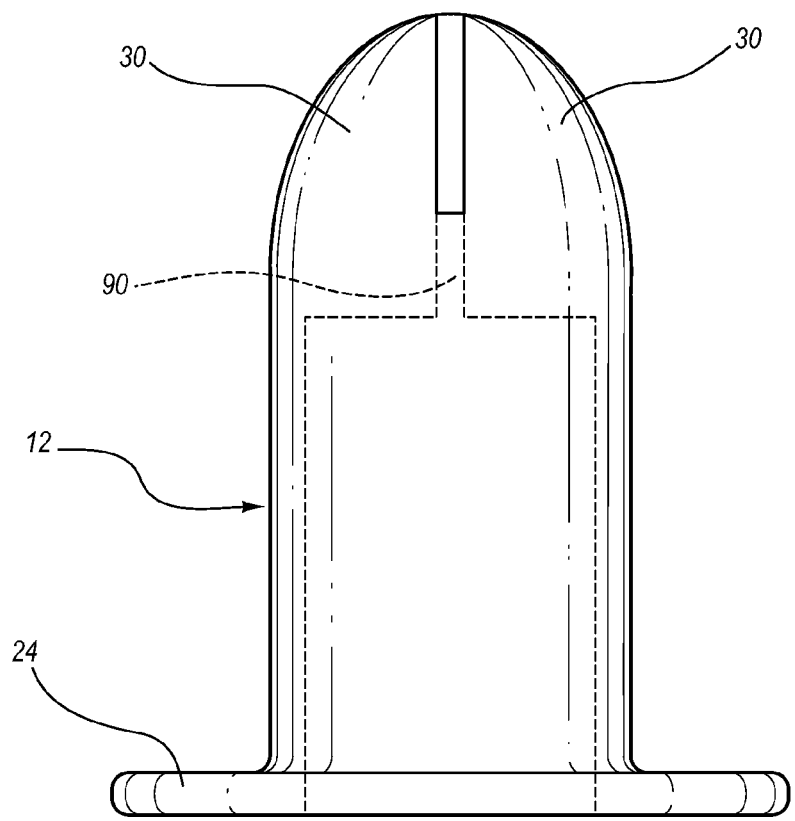
Figure 10:
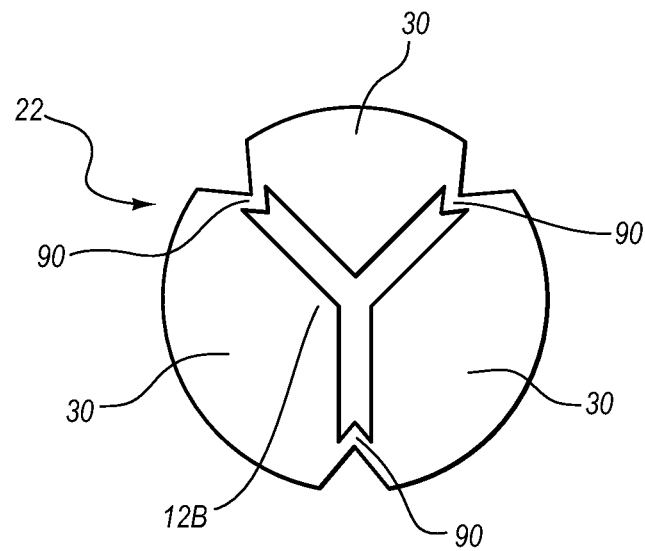
FIG. 10 is an end view of a feeding device including webbing between the bolster arms of the internal bolster according to one embodiment.

Reference is now made to FIGS. 9A and 9B, which show that in one embodiment webbing 90 is included between adjacent internal bolster arms 30. Formed of the same material from which the bolster arms 30 are formed, e.g., silicone, the webbing 90 helps in one embodiment to form a seal about the stoma when the internal bolster 22 is deployed into its expanded state (FIG. 1C). FIG. 10 shows that the webbing in one embodiment can be folded so as to provide relatively more webbing for ease in bolster arm expansion during internal bolster deployment. These and other modifications to the particular internal bolster configuration are thus contemplated.

Figure 11A:
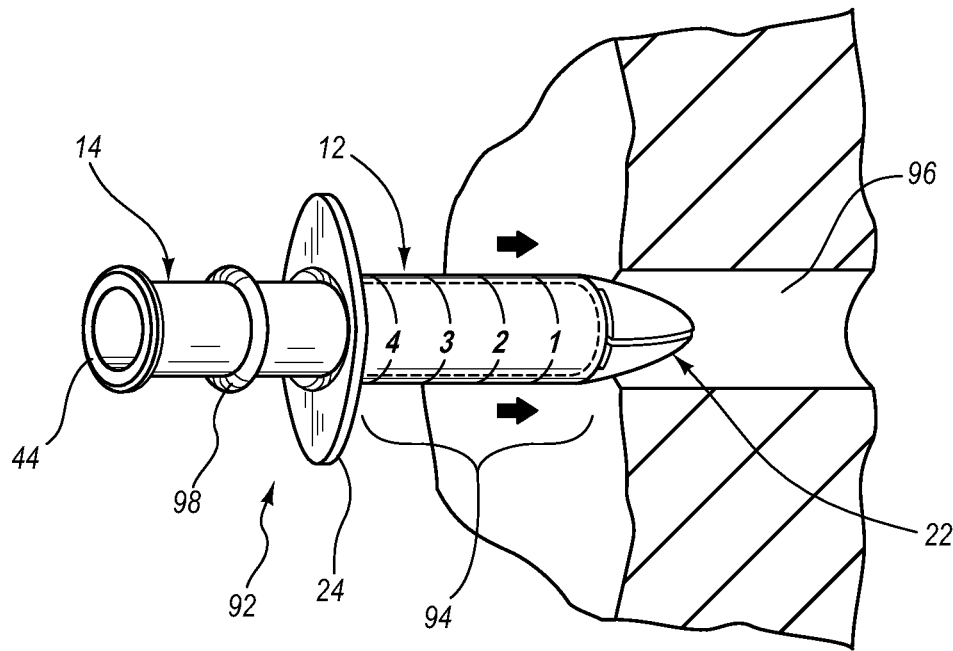
FIGS. 11A and 11B are side views of a feeding device including a stoma measuring system in accordance with one embodiment.
Figure 11B:
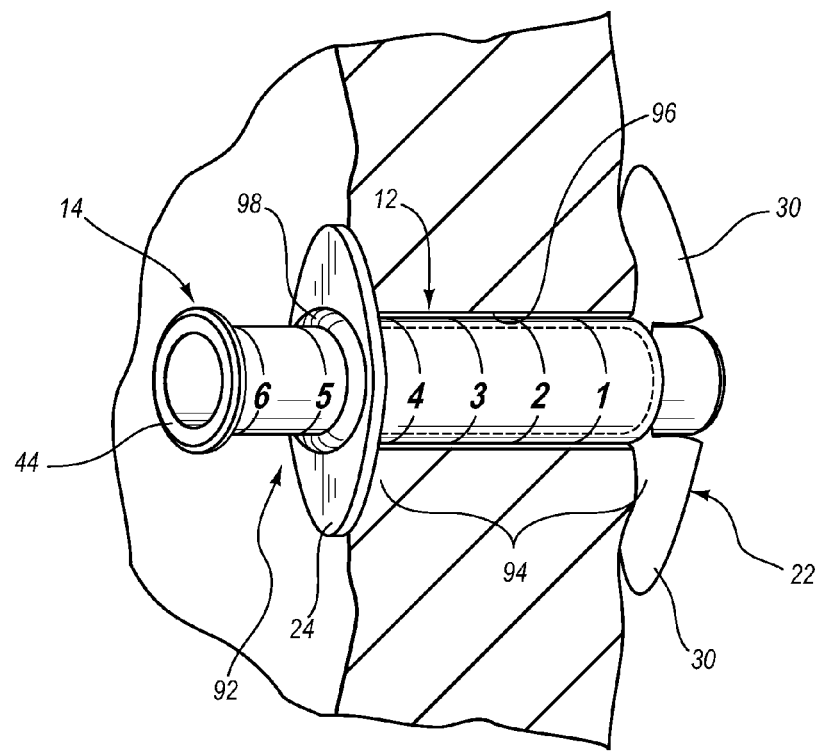

FIGS. 11A and 11B show that one embodiment of the present invention enables the internal bolster design to be employed in a stoma measuring device for measuring the length of a stoma, such as a stoma 96 shown in FIG. 11A, during feeding device replacement procedures, for instance. In particular, a measuring device 92 is shown, including a plurality of graduations 94 disposed on the bolster tube 12 so as to be visible by a user of the measuring device. During use, the measuring device 92 is inserted into the stoma 96, the internal bolster 22 deployed, and the device pulled proximally so as to seat the internal bolster against the inner entrance to the stoma, as shown in FIG. 11B. This establishes the zero point of the stoma depth. The user can then note the length of the stoma 96 by noting the number of graduation 94 of the measuring device 92 at the stoma exit site on the skin surface, thus indicating the length of the stoma 96. A second plunger stop 98 can be used in one embodiment to prevent full insertion of the plunger 14 into the cavity 20 of the bolster tube 12.

Figures 12A, 12B:
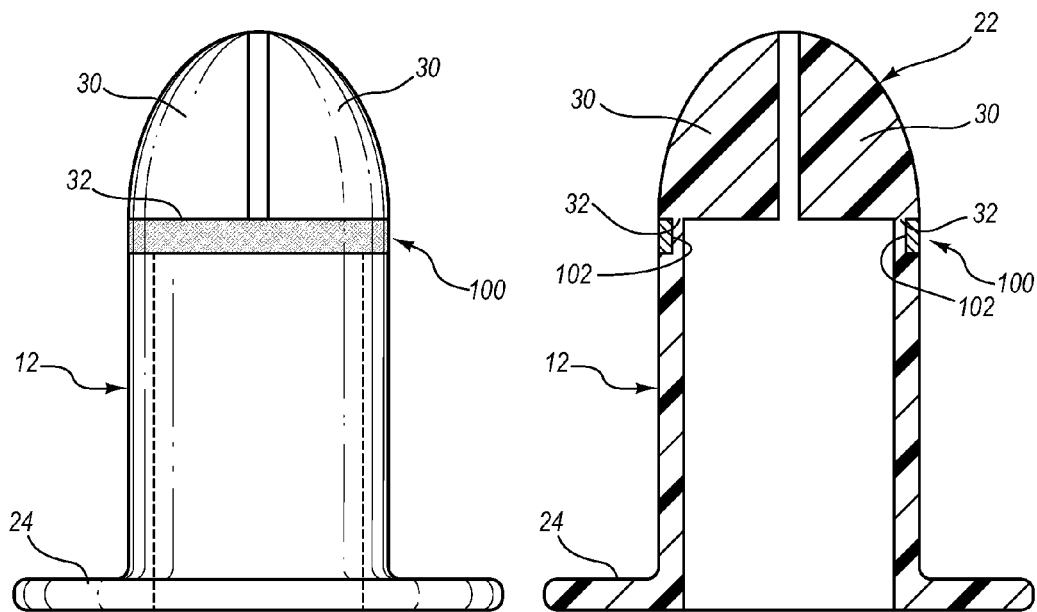
FIGS. 12A and 12B are side views of an internal bolster of the feeding device of FIG. 1A including a reinforcing collar and a notch for its positioning, according to one embodiment.

FIGS. 12A and 12B show that in one embodiment an annular reinforcing collar 100 including stainless steel or other suitably hard and biocompatible metal or substance can be added about the base of the bolster arms 30 proximate the hinge point 32 on the bolster tube 12 so as to fortify the retention force of the internal bolster 22 when deployed in a stoma. The collar 100 in one embodiment is seated in an annular notch 102 in one embodiment and as shown in FIG. 12B, though in other embodiments other reinforcement schemes can be used. For instance, the collar can be other than round to fit on bolster tubes with non-circular cross sectional shapes, or can include only a portion of a circular ring.

Figure 13A:
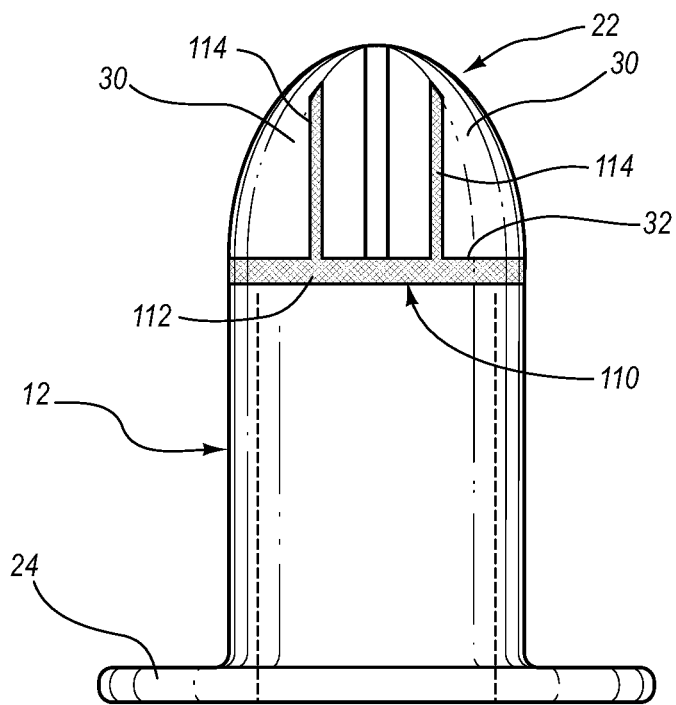
FIGS. 13A and 13B are side and end views, respectively, of an internal bolster of the feeding device of FIG. 1A including a reinforcement structure, according one embodiment.
Figure 13B:
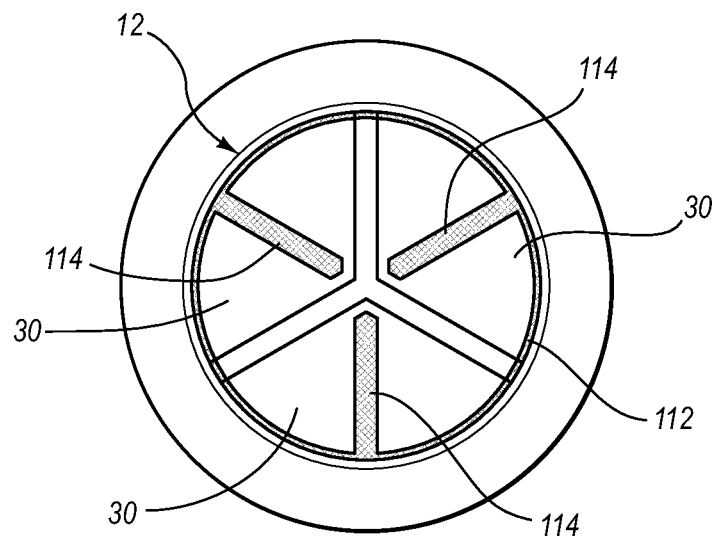

FIGS. 13A and 13B give an example of another reinforcement scheme according to one embodiment, wherein a reinforcement structure 110 includes a collar 112 similar to that shown in FIG. 12A and a plurality of spines 114 that each extend into one of the bolster arms 30 so as to provide added strength to the internal bolster 22. The spines 114 are bendable at the point of connection with the collar 112 in the present embodiment to enable pivoting of each bolster arm 30 about the hinge point 32. Stainless steel or other suitable material can be used for the collar 112 and spines 114. These and other reinforcement schemes are therefore contemplated.

Figure 14A:
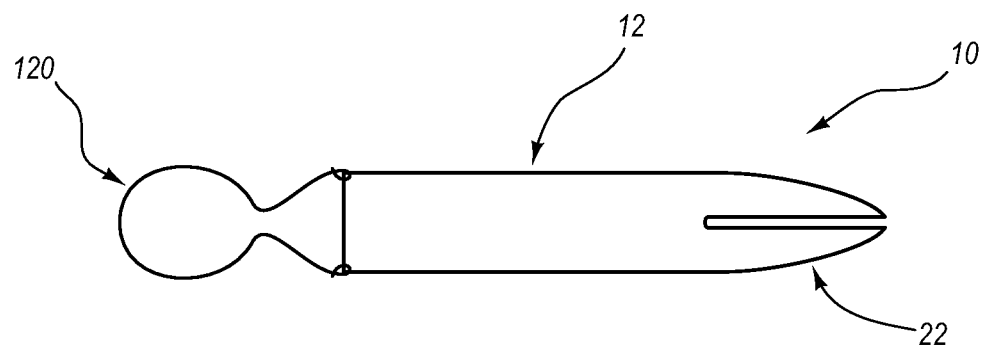
FIGS. 14A-14D are various views of a feeding device configured for initial endoscopic placement, according to one embodiment.
Figure 14B:
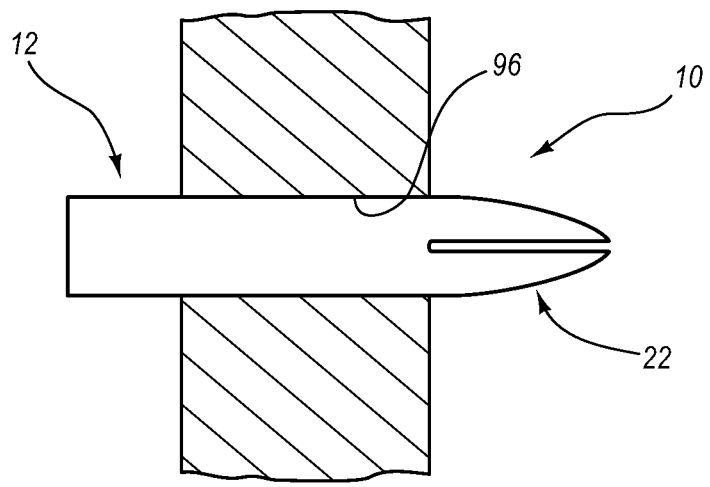
Figure 14C:
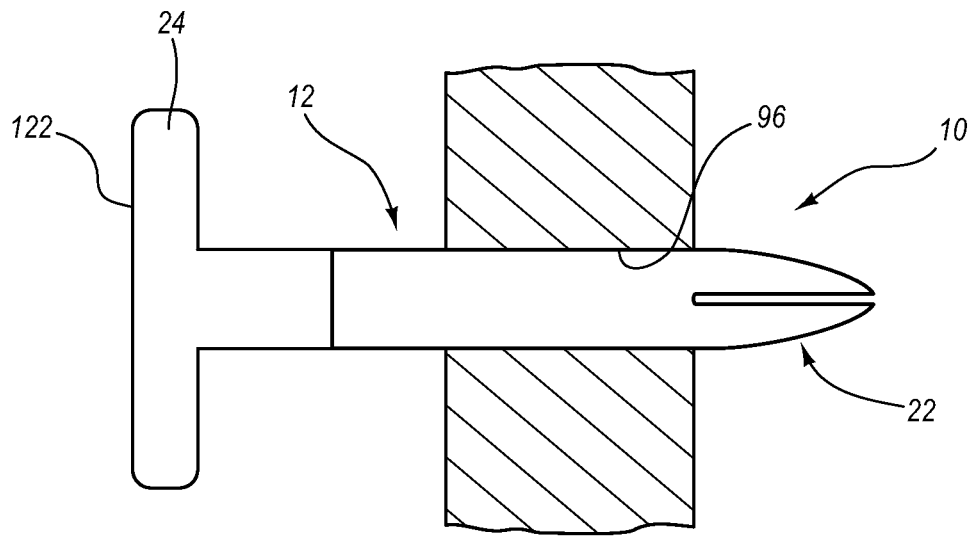
Figure 14D:
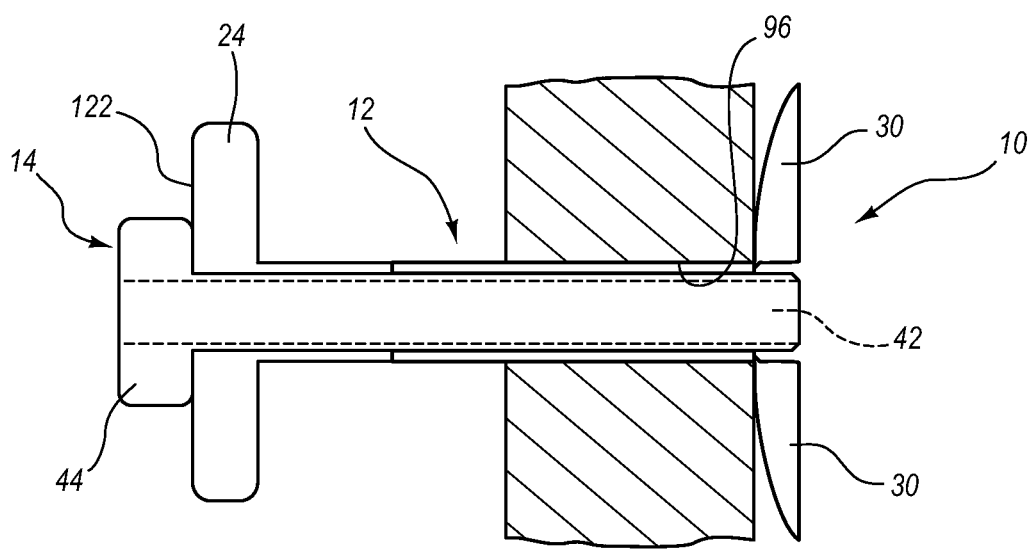
Figure 15:
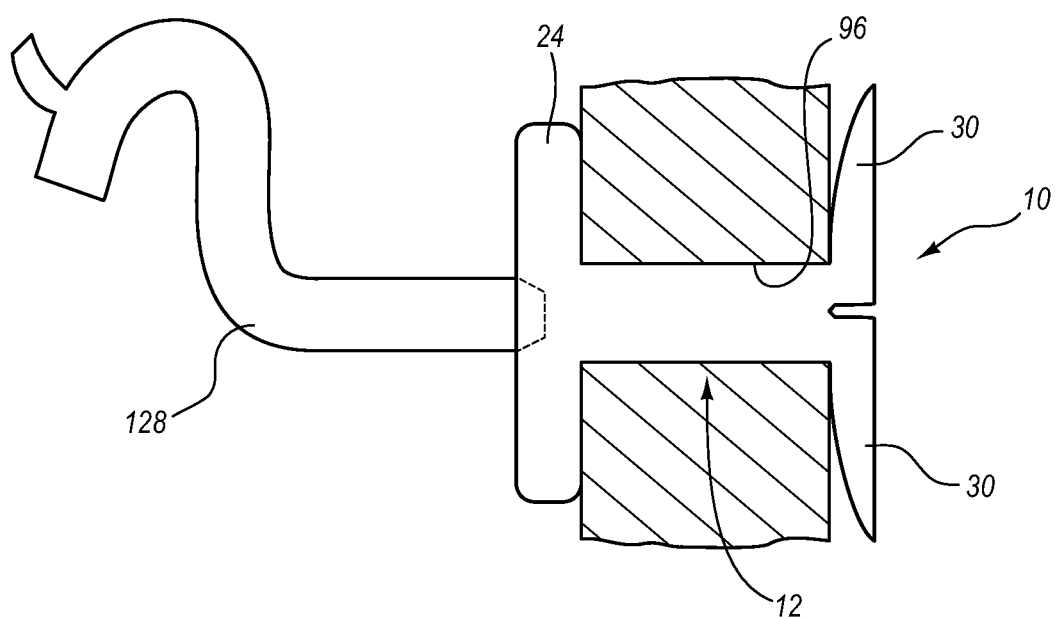
FIG. 15 is a side view of a tubing extension for providing enteral nutrition to a patient that can be employed with a feeding device such as that shown in FIG. 1A in accordance with one embodiment.

Reference is now made to FIGS. 14A-14D. In previous embodiments the internal bolster was contemplated for use, among other things, in connection with a replacement feeding device, i.e., a device replacing another device that was previously disposed within a stoma. In one embodiment, the feeding device 10 can also be configured as an initial placement feeding device for initial insertion into a patient. So configured, the feeding device 10 includes a snare 120 on the proximal end of the bolster tube 12, which snare can be removed after the bolster tube has been endoscopically inserted into the patient and positioned within the stoma 96, as shown in FIG. 14B. An adapter 122 is then attached to the proximal end of the bolster tube 12, which includes the flange 24, as shown in FIG. 14C. The plunger 14 can then be inserted into the bolster tube cavity 20 to engage and deploy the internal bolster 22, as shown in FIG. 14D. In one embodiment, it is appreciated that the adapter 122 and the plunger 14 can be connected to or integrated with one another so as to be attachable as a unit to the bolster tube 12. FIG. 15 shows that in one embodiment, the feeding device 10 can attach to, or have integrally formed therewith, an external extension tube 128 for use with enteral feeding.

Figure 16A:
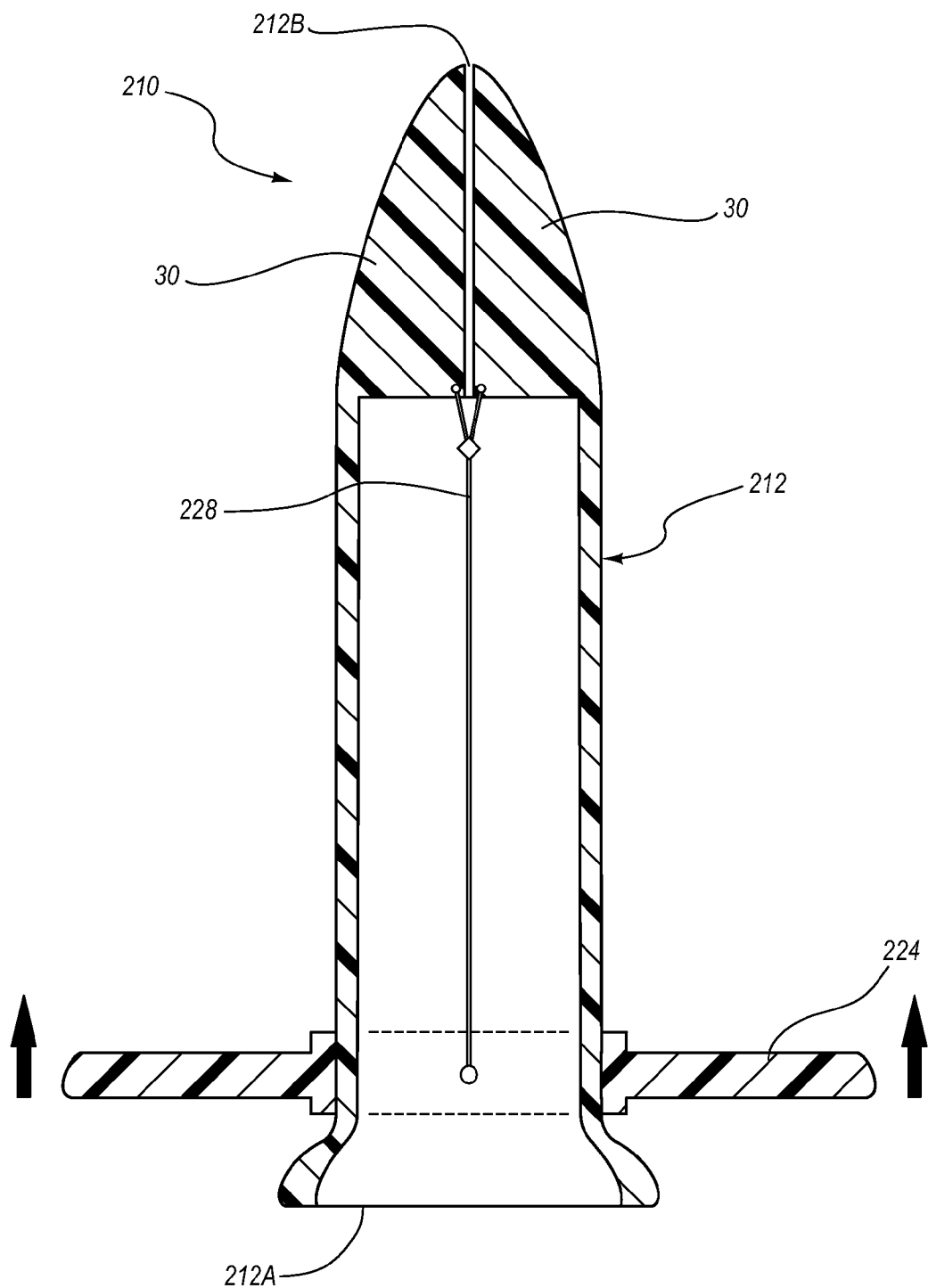
FIGS. 16A and 16B are cross sectional views of a feeding device including an internal bolster configured in accordance with one embodiment.

Reference is now generally made to FIGS. 16A-17C, which depict other examples of means for selectively moving bolster arms of an internal bolster between the first and second positions in order to selectively deploy the internal bolster for securing an indwelling medical device. In particular, FIGS. 16A and 16B depict a feeding device 210 with an extensible internal bolster according to one embodiment. The feeding device 210 includes a hollow body 212 defining a proximal end 212A and a distal end 212B. A flange 224 is attached to the body 212 and is slidable with respect thereto. Wires 228 are attached to the flange 224 and extend along the body so as to operably attach to a respective one of the extensible bolster arms 30, which are attached to the body at a hinge point via living hinges or other suitable connective scheme. The wires 228 can include a nickel-titanium alloy commonly known as nitinol, or other suitable metal or material.

Figure 16B:
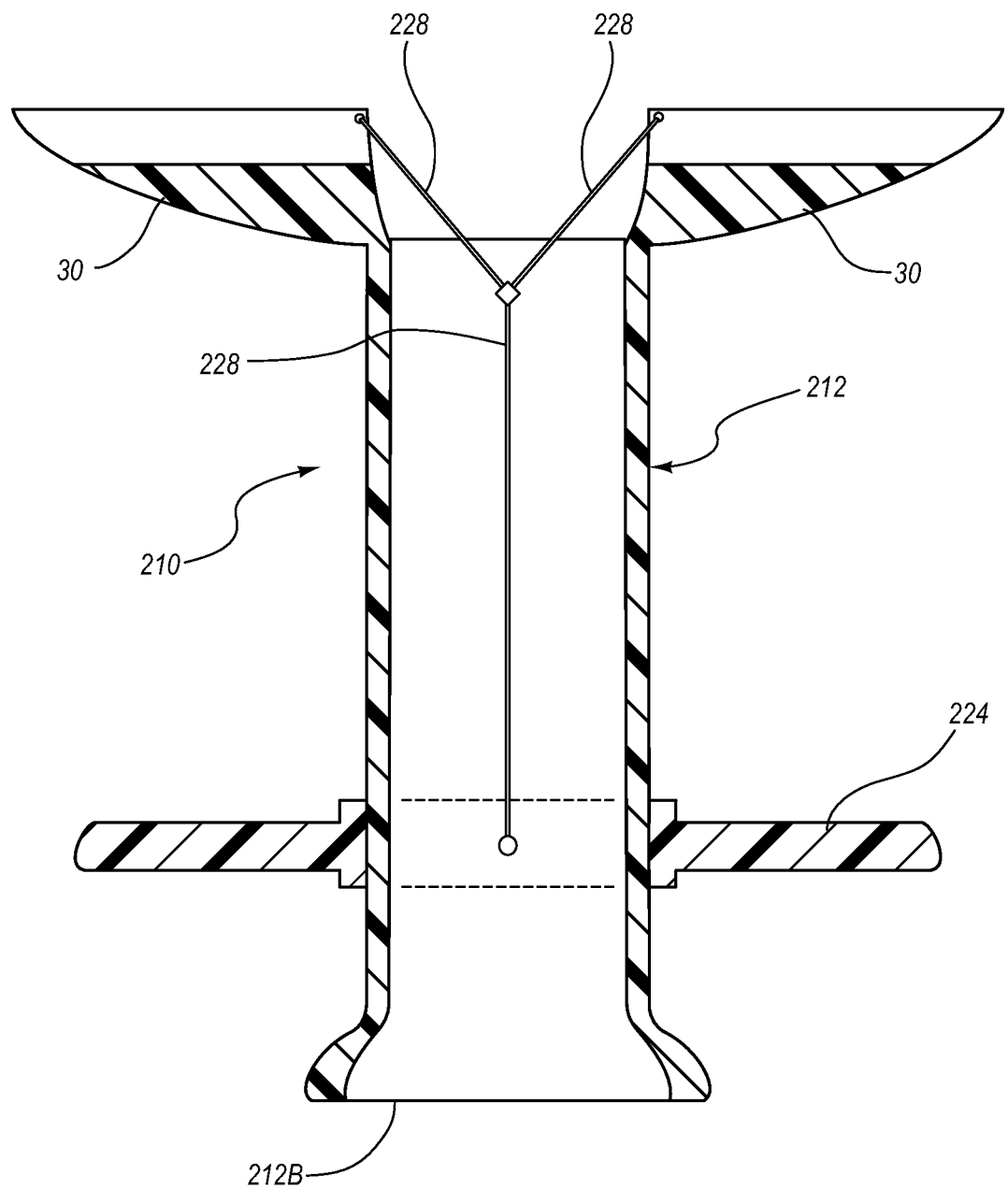

As shown in FIG. 16B, the flange 224 acts as a trigger for deploying the bolster arms 30, wherein sliding or other movement of the flange toward the distal end 212B of the body 212 causes the wires 228 to actuate the bolster arms and extend them into their deployed position. Note that the wires 228 are sufficiently rigid to actuate the bolster arms. It is further appreciated that other structures can be used to interconnect the bolster arms to the flange or other suitable component. Correspondingly, proximal movement of the flange 224 correspondingly causes the bolster arms 30 to contract back to their original un-deployed position. Thus, it is seen that multiple configurations exist for deployment of the internal bolster.

Figure 17A:
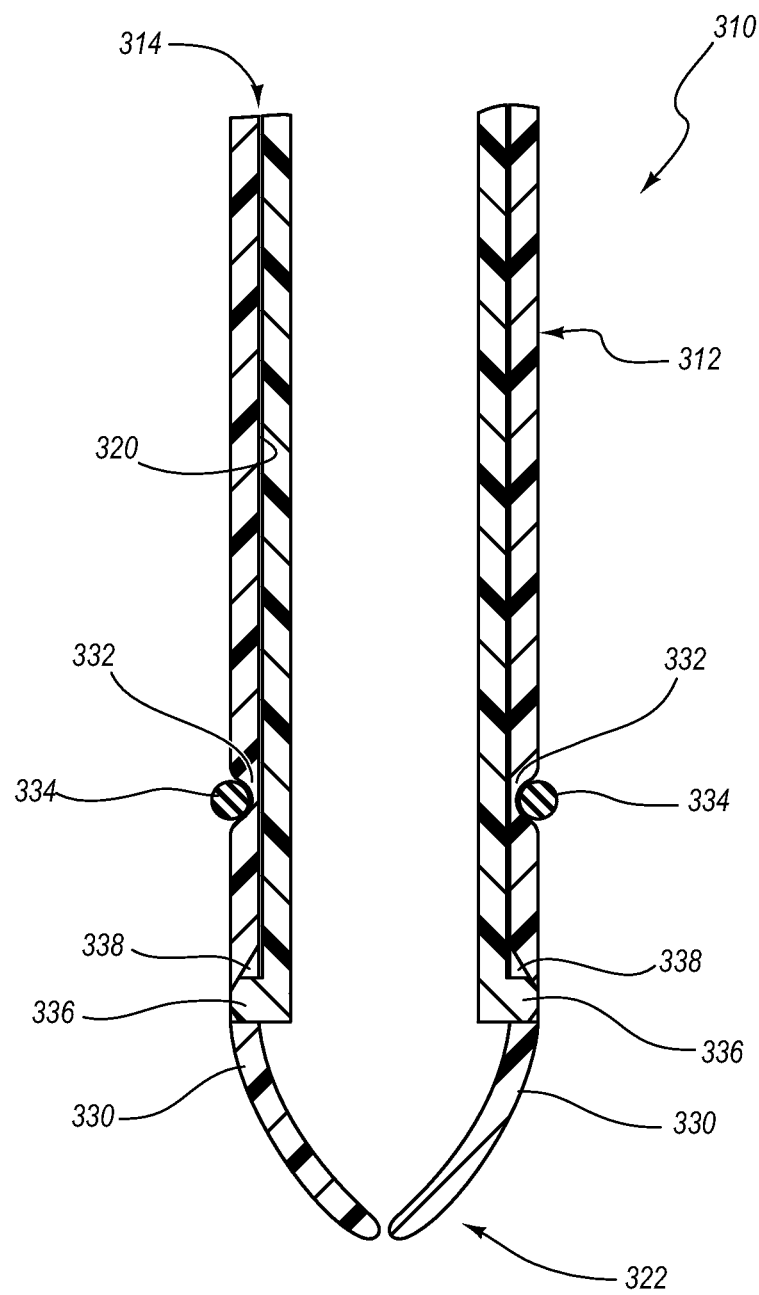
FIGS. 17A-17C are various views of a feeding device including an internal bolster configured in accordance with one embodiment.
Figure 17B:
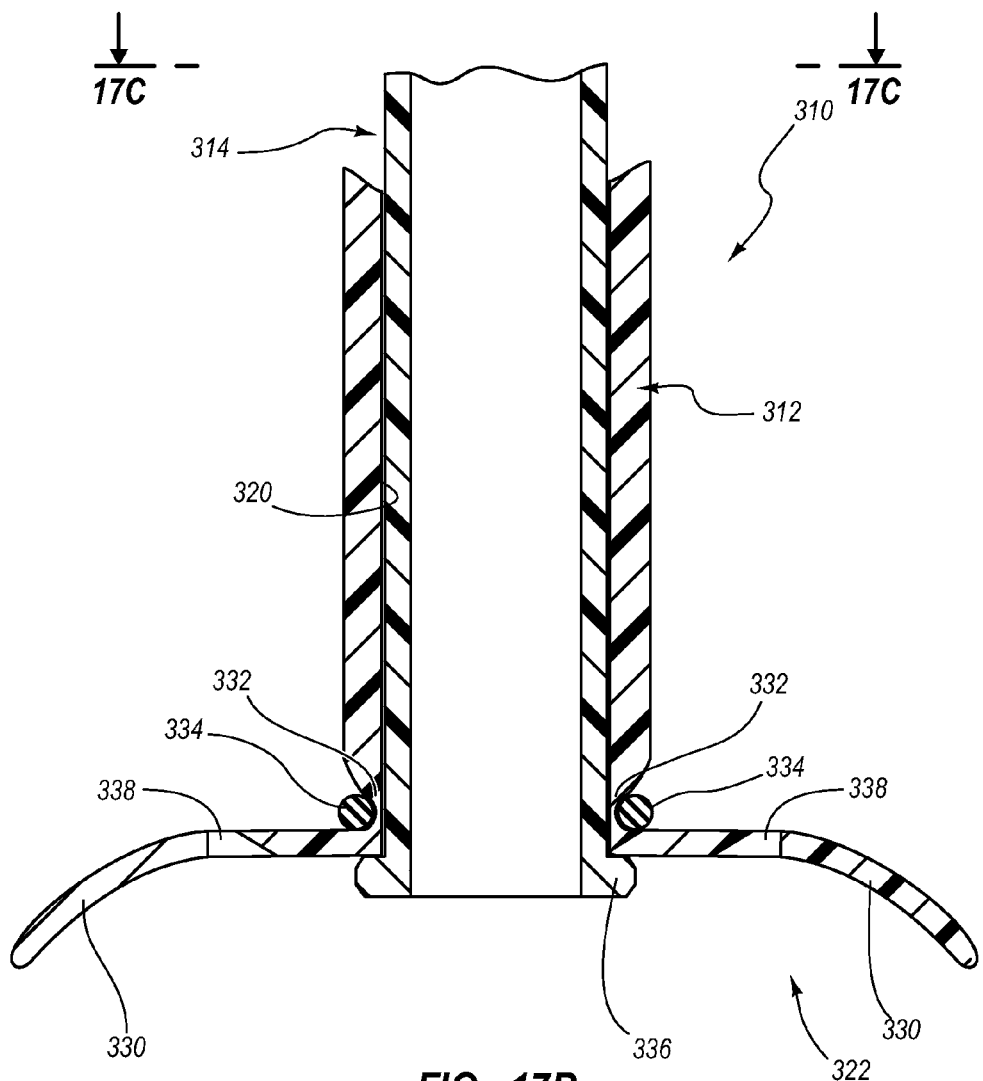
Figure 17C:
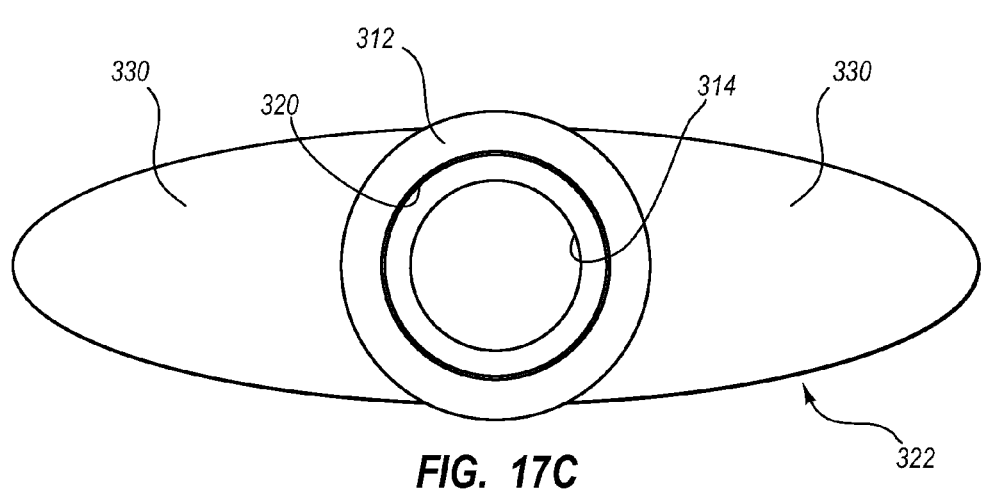

FIGS. 17A-17C depict a feeding device 310 including another example of means for selectively moving bolster arms of an internal bolster between the first and second positions, according to one embodiment. In particular, the feeding device 310 includes a bolster tube 312 that slidably receives a plunger 314 in a cavity 320 thereof, similar to previous embodiments. An internal bolster 322 is included on the distal end of the bolster tube 312, and includes two extensible bolster arms 330 attached to the bolster tube at hinge points 332 via living hinges for instance, though more or fewer arms can be employed if desired. A non-stretching O-ring 334 is positioned proximate the living hinges 332 on an outer portion of the bolster tube 312 to prevent the bolster tube from expanding in diameter during internal bolster deployment. The plunger 314 includes a radially extending annular lip 336 at its distal end.

FIG. 17A shows the feeding device 310 in a first un-deployed position, wherein the bolster arms 330 of the internal bolster 322 are un-extended. In this position, the annular lip 336 is received into an annular cutout 338 defined by each of the bolster arms 330. To deploy the internal bolster 322 from the un-deployed position shown in FIG. 17A, the plunger 314 is pulled proximally with respect to the bolster tube 312, which causes the annular lip 336 to be removed from the cutouts 338 and press against the bolster arms 330. This causes the bolster arms 330 to expand into the second deployed position shown in FIG. 17B. The O-ring 334 assists in maintaining the deployed position of the bolster arms 330. Reverse movement of the plunger 314 will correspondingly enable the annular lip 336 to re-seat within the cutouts 338 and allow the bolster arms to return to their un-deployed position, such as for insertion or removal from the stoma of a patient.

FIGS. 18A-18E depict a feeding device 410 including an extensible internal bolster according to yet another embodiment. As shown, the feeding device 410 includes a bolster tube 412 that slidably receives a plunger 414 in a cavity 420 thereof, as in previous embodiments. An internal bolster 422 is included on the feeding device 410 and includes two foldable flaps 430. The flaps 430 include a joined distal end attached to a distal end of one or more tethers 434, and a proximal end attached to a distal portion of the plunger 414. The two tethers 434 each extend from the distal end of the flaps 430 proximally to a portion of the bolster tube 412 proximal to the internal bolster 422. So configured, the flaps 430 and tethers 434 are commonly connected at a distal end of the internal bolster 422, as seen in FIGS. 18A-18E, yet respectively separated proximally therefrom so as to be independently movable with respect to one another. Note that the size, shape, and number of flaps and tethers can vary from what is explicitly shown and described herein.

Figure 18A:
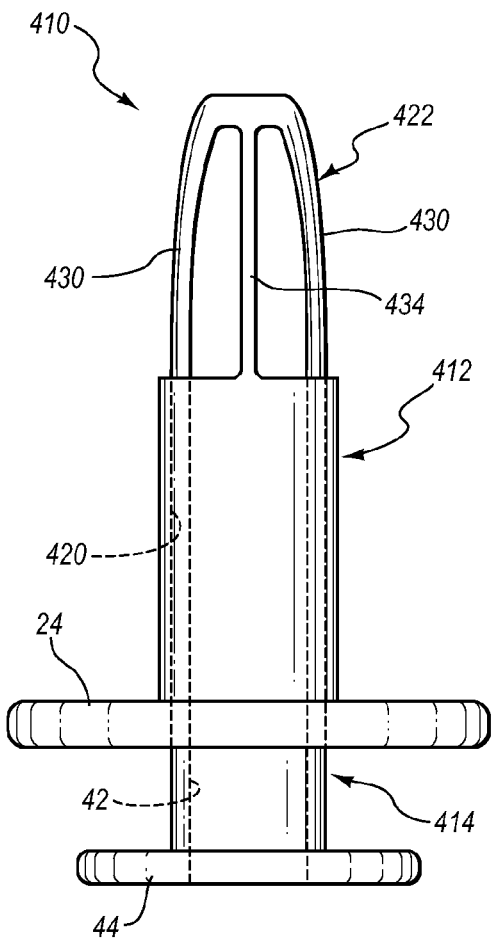
FIGS. 18A-18E are various views of a feeding device including an internal bolster configured in accordance with one embodiment.
Figure 18B:
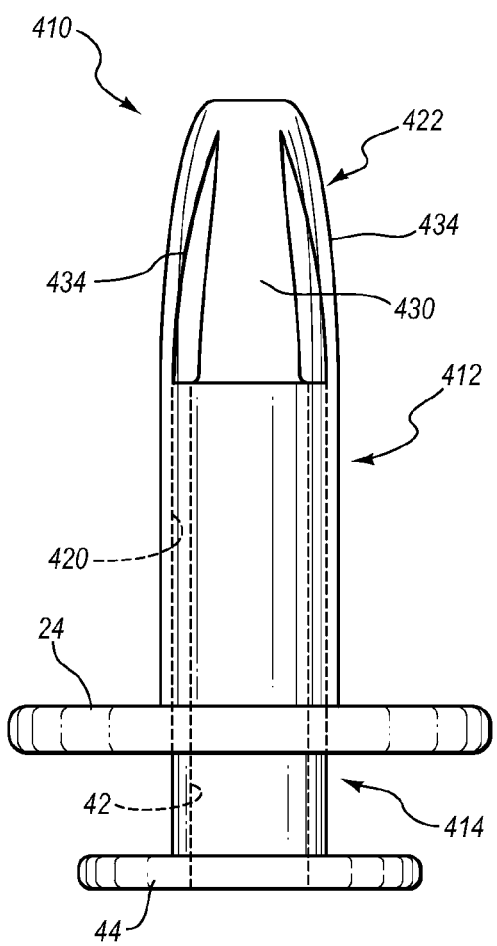
Figure 18C:
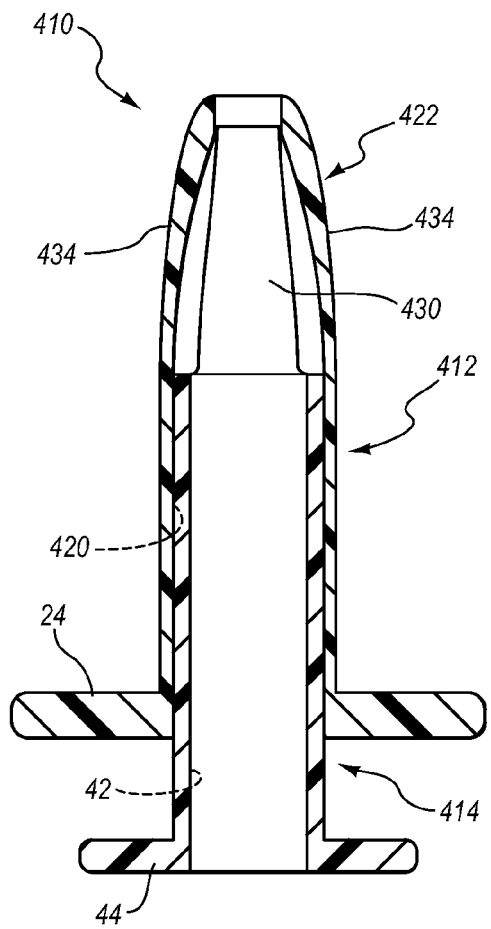
Figure 18D:
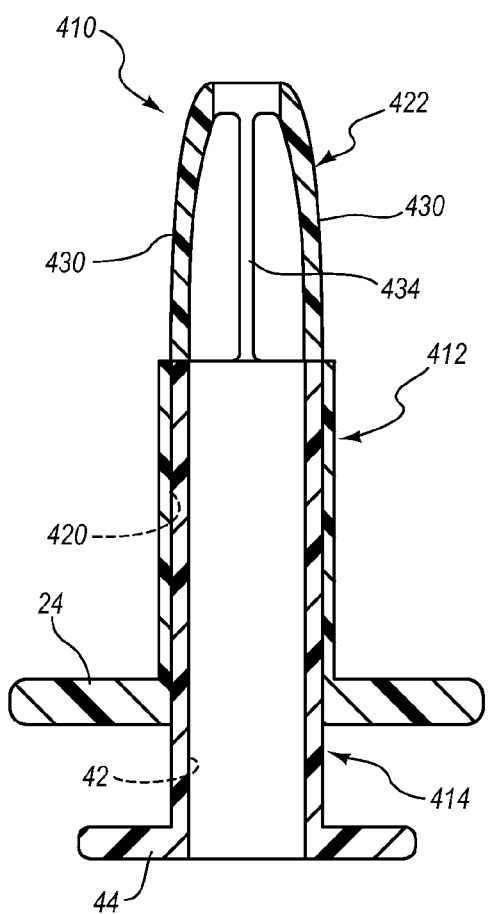
Figure 18E:
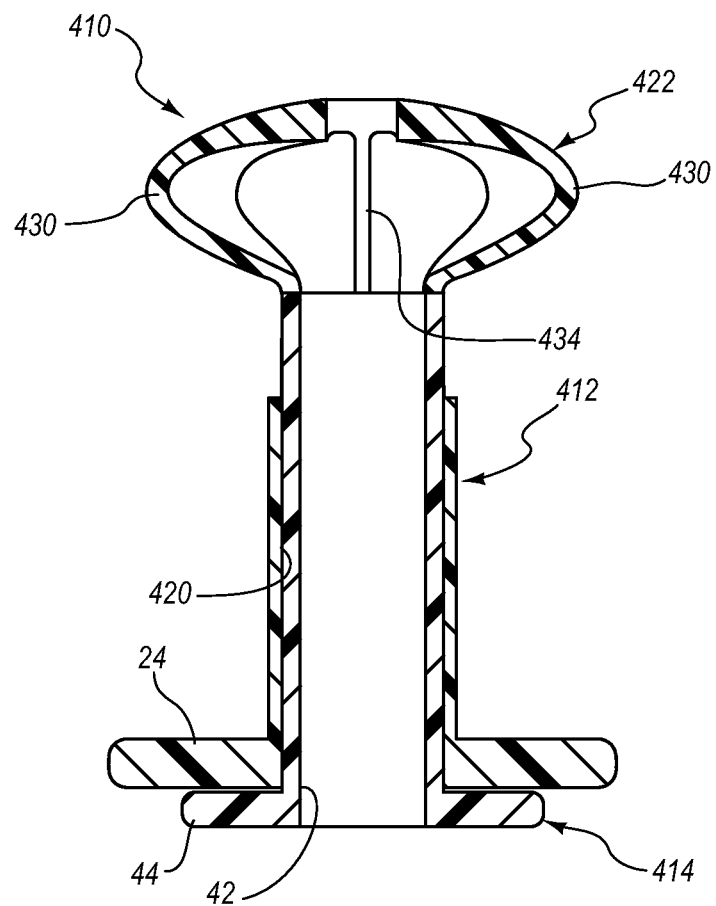

To actuate the internal bolster 422 of the feeding device 410, the plunger 414 is pushed distally. The tethers 434 prevent distal movement of the internal bolster 422 during movement of the plunger 414. This causes the flaps 430 to bend outward, as shown in FIG. 18E, thus forming an internal bolster for securing the feeding device 410 in a stoma of a patient, for instance. The process may be reversed to collapse the internal bolster 422 and remove the feeding device 410 from the patient. A suitable means for locking axial plunger movement relative to the bolster tube 412 can be included to maintain the internal bolster 422 in its deployed state.

Note that the principles described herein can be expanded while still residing within the scope of the present disclosure. For instance, the hollow plunger described above can be include other feeding channel configurations or can be other than cylindrically shaped in other embodiments.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical device comprising:
a tubular body;
at least two bolster arms, each including a first end hingedly connected to a distal end of the tubular body and a free second end, wherein the at least two bolster arms are selectively deployable between a first position wherein the at least two bolster arms are substantially in-line with an axis of the medical device and a second position wherein the at least two bolster arms are substantially deflected from the axis of the medical device to enable securement of the medical device within a patient's body;
webbing disposed between adjacent bolster arms;
a plunger slidable within the tubular body to move the bolster arms between the first position and the second position; and
a locking mechanism configured to lock axial movement of the plunger relative to the tubular body.

2. The medical device according to claim 1, wherein the at least two bolster arms are positioned contiguously with one another and define a tapered atraumatic distal end of the medical device when in the first position, and wherein the bolster arms move radially outward with respect to one another in unison when deployed from the first to the second position.

3. The medical device according to claim 1, wherein, in the second position, the webbing is configured to form a seal about a stoma in the patient's body when secured therewithin.

4. The medical device according to claim 1, wherein the at least two bolster arms when in the first position are contiguous with one another and together define an outer diameter that does not exceed an outer diameter of a distal half of the medical device, and wherein the free second end of one of the at least two bolster arms is radially spread apart from the free second end of another of the at least two bolster arms when in the second position to secure a distal portion of the medical device within the patient's body after insertion thereof.

5. The medical device according to claim 1, wherein the locking mechanism includes at least one extended surface included on one of the plunger and tubular body, the at least one extended surface seating within a corresponding recess defined on one of the plunger and the tubular body when the plunger has deployed the at least two bolster arms to the second position.

6. The medical device according to claim 1, wherein the locking mechanism includes threads correspondingly defined on the plunger and the tubular body, the plunger being threadably received within the tubular body so as to deploy the at least two bolster arms to the second position.

7. The medical device according to claim 1, wherein the locking mechanism includes at least one pin insertable through the tubular body to engage the plunger so as to prevent movement thereof.

8. The medical device according to claim 1, wherein the plunger includes a central channel configured as a feeding channel through which a patient may be fed.

9. The medical device according to claim 8, wherein the plunger includes an engagement surface for deploying the at least two bolster arms from the first position to the second position, the engagement surface including a radially extending annular lip proximate a distal end of the plunger, and wherein the plunger is positioned such that the first end of each of the at least two bolster arms is between the annular lip and an O-ring disposed about the medical device in the second position.

10. The medical device according to claim 1, wherein each of the at least two bolster arms is hingedly attached to the tubular body via a living hinge, and wherein the bolster arms cover a distal end opening of the tubular body when in the first position, the distal end opening being at least partially uncovered in the second position.

11. The medical device according to claim 1, further comprising a reinforcing collar disposed radially about at least a portion of the distal end of the tubular body.

12. The medical device according to claim 11, further comprising a plurality of spines, and at least two bolster arms including at least one spine of the plurality of spines.

13. The medical device according to claim 1, further comprising stoma measuring graduations on an outer surface of the tubular body so as to enable a measurement of a length of a stoma through which the medical device is positioned.

14. A method, comprising:
providing a medical device comprising:
a tubular body;
a first bolster arm hingedly connected to a distal end of the tubular body;
a second bolster arm hingedly connected to the distal end of the tubular body;
a plunger slidable within the tubular body to move the first bolster arm and the second bolster arm between a first closed configuration in which the first bolster arm and the second bolster arm are positioned close together to a second open configuration in which the first bolster arm and the second bolster arm are spaced apart; and
a locking mechanism configured to lock axial movement of the plunger relative to the tubular body;
positioning the medical device in a patient's body through a stoma, a distal portion of the medical device positioned inside the patient's body, wherein the positioning is performed while the first bolster arm and the second bolster arm are in the first closed configuration;
deploying the first bolster arm and the second bolster arm to the second open configuration to secure the distal portion of the medical device within the patient's body; and
locking the locking mechanism such that the plunger is locked in a position that holds the first bolster arm and the second bolster arm in the second open configuration.

15. The method according to claim 14, wherein the medical device includes stoma measuring graduations so as to enable a measurement of a length of the stoma through which the medical device is positioned, further comprising measuring the length of the stoma.

16. The method according to claim 14, wherein the plunger includes a central channel configured as a feeding channel, further comprising feeding the patient through the central channel.

17. The method according to claim 14, wherein the locking mechanism includes threads correspondingly defined on the plunger and the tubular body, and wherein locking the locking mechanism includes threadably engaging the threads of the plunger and the tubular body.

18. The method according to claim 14, wherein the locking mechanism includes at least one pin, and wherein locking the locking mechanism includes positioning the pin through the tubular body such that the pin engages the plunger and prevents movement thereof.

19. A medical device comprising:
a tubular body;
at least two bolster arms, each including a first end hingedly connected to a distal end of the tubular body and a free second end, wherein the at least two bolster arms are selectively deployable between a first position wherein the at least two bolster arms are substantially in-line with an axis of the medical device and a second position wherein the at least two bolster arms are substantially deflected from the axis of the medical device to enable securement of the medical device within a patient's body;
a plunger slidable within the tubular body to move the bolster arms between the first position and the second position, the plunger comprising:
a central channel configured as a feeding channel through which a patient may be fed; and
an engagement surface for deploying the at least two bolster arms from the first position to the second position, the engagement surface including a radially extending annular lip proximate a distal end of the plunger,
wherein the plunger is positioned such that the first end of each of the at least two bolster arms is between the annular lip and an O-ring disposed about the medical device in the second position; and
a locking mechanism configured to lock axial movement of the plunger relative to the tubular body.

20. A medical device comprising:
a tubular body;
a reinforcing collar disposed radially about at least a portion of a distal end of the tubular body;
at least two bolster arms, each including a first end hingedly connected to the distal end of the tubular body and a free second end, wherein the at least two bolster arms are selectively deployable between a first position wherein the at least two bolster arms are substantially in-line with an axis of the medical device and a second position wherein the at least two bolster arms are substantially deflected from the axis of the medical device to enable securement of the medical device within a patient's body;
a plurality of spines, each of the at least two bolster arms including at least one spine of the plurality of spines;
a plunger slidable within the tubular body to move the bolster arms between the first position and the second position; and
a locking mechanism configured to lock axial movement of the plunger relative to the tubular body.

21. A medical device comprising:
a tubular body;
at least two bolster arms, each including a first end hingedly connected to a distal end of the tubular body and a free second end, wherein the at least two bolster arms are selectively deployable between a first position wherein the at least two bolster arms are substantially in-line with an axis of the medical device and a second position wherein the at least two bolster arms are substantially deflected from the axis of the medical device to enable securement of the medical device within a patient's body;
at least one elongate wire member interconnecting each of the at least two bolster arms with a movable trigger external to the patient's body, wherein movement of the trigger causes the wire member to reversibly deploy the at least two bolster arms from the first position to the second position; and
a locking mechanism configured to lock axial movement of the plunger relative to the tubular body.

* * * * *